US011344373B2

(12) United States Patent
Gopinath et al.

(10) Patent No.: US 11,344,373 B2
(45) Date of Patent: May 31, 2022

(54) STENT EXPANSION DISPLAY, SYSTEMS, AND METHODS

(71) Applicant: LIGHTLAB IMAGING, INC., Westford, MA (US)

(72) Inventors: Ajay Gopinath, Scarborough, MA (US); Kyle Savidge, Medford, MA (US); Robert Steinbrecher, Wrentham, MA (US)

(73) Assignee: LightLab Imaging, Inc., Westford, MA (US)

( * ) Notice: Subject to any disclaimer, the term of this patent is extended or adjusted under 35 U.S.C. 154(b) by 444 days.

(21) Appl. No.: 16/425,709

(22) Filed: May 29, 2019

(65) Prior Publication Data
US 2019/0365480 A1   Dec. 5, 2019

Related U.S. Application Data

(60) Provisional application No. 62/677,623, filed on May 29, 2018.

(51) Int. Cl.
*A61B 5/00*     (2006.01)
*A61B 34/20*    (2016.01)
(Continued)

(52) U.S. Cl.
CPC ............ *A61B 34/20* (2016.02); *A61B 5/0066* (2013.01); *A61B 5/021* (2013.01); *A61B 5/026* (2013.01);
(Continued)

(58) Field of Classification Search
CPC ....... A61B 34/20; A61B 5/0066; A61B 5/021; A61B 5/026; A61B 5/6852; A61B 5/6876;
(Continued)

(56) References Cited

U.S. PATENT DOCUMENTS

| 5,321,501 A | 6/1994 | Swanson et al. |
| 5,459,570 A | 10/1995 | Swanson et al. |

(Continued)

FOREIGN PATENT DOCUMENTS

| EP | 3053505 | 8/2016 |
| EP | 3171763 | 5/2017 |
| WO | 2016187231 | 11/2016 |

OTHER PUBLICATIONS

Wang et al. "3D assessment of stent cell size and side branch access in intravascular optical coherence tomographic pullback runs" Computerized Medical Imaging and Graphics 38:113-122 (2014).
(Continued)

*Primary Examiner* — Joel Lamprecht
(74) *Attorney, Agent, or Firm* — Lerner, David, Littenberg, Krumholz & Mentlik, LLP

(57) ABSTRACT

In part, the disclosure relates to systems and methods to assess stent/scaffold expansion in a vessel on an expedited time scale after stent/scaffold placement and expansion. In one embodiment, the method generates a first representation of a stented segment of the blood vessel indicative of a level of stent expansion; determines using the detected stent struts, a first end of the stent and a second end of the stent; and generate a second representation of the segment of the blood vessel by interpolating a lumen profile using an offset distance from the first end and the second end.

25 Claims, 10 Drawing Sheets
(6 of 10 Drawing Sheet(s) Filed in Color)

(51) Int. Cl.
    *A61B 34/00*     (2016.01)
    *A61B 90/00*     (2016.01)
    *A61B 5/021*     (2006.01)
    *A61B 5/026*     (2006.01)
    *A61B 6/12*     (2006.01)
    *A61B 6/00*     (2006.01)
    *A61B 8/08*     (2006.01)
    *A61F 2/95*     (2013.01)
    *A61B 34/10*     (2016.01)

(52) U.S. Cl.
CPC .......... *A61B 5/6852* (2013.01); *A61B 5/6876* (2013.01); *A61B 6/12* (2013.01); *A61B 6/504* (2013.01); *A61B 8/0841* (2013.01); *A61B 34/25* (2016.02); *A61B 90/37* (2016.02); *A61F 2/95* (2013.01); *A61B 2034/105* (2016.02); *A61B 2090/364* (2016.02); *A61B 2090/376* (2016.02); *A61B 2090/378* (2016.02); *A61B 2090/3735* (2016.02); *A61B 2505/05* (2013.01)

(58) Field of Classification Search
CPC .......... A61B 6/12; A61B 6/504; A61B 8/0841; A61B 34/25; A61B 90/37; A61B 2034/105; A61B 2090/364; A61B 2090/3735; A61B 2090/376; A61B 2090/378; A61B 2505/05; A61B 5/0035; A61B 5/02007; A61B 5/0215; A61B 5/1076; A61B 5/4851; A61F 2/95; A61F 2/90; A61F 2240/008; G06T 2207/30004; G06T 2207/30101; G06T 7/13; G06T 7/62

See application file for complete search history.

(56) References Cited

U.S. PATENT DOCUMENTS

| | | |
|---|---|---|
| 5,465,147 A | 11/1995 | Swanson |
| 5,509,093 A | 4/1996 | Miller et al. |
| 5,619,368 A | 4/1997 | Swanson |
| 5,748,598 A | 5/1998 | Swanson et al. |
| 5,784,352 A | 7/1998 | Swanson et al. |
| 5,956,355 A | 9/1999 | Swanson et al. |
| 6,111,645 A | 8/2000 | Tearney et al. |
| 6,134,003 A | 10/2000 | Tearney et al. |
| 6,160,826 A | 12/2000 | Swanson et al. |
| 6,191,862 B1 | 2/2001 | Swanson et al. |
| 6,282,011 B1 | 8/2001 | Tearney et al. |
| 6,421,164 B2 | 7/2002 | Tearney et al. |
| 6,445,939 B1 | 9/2002 | Swanson et al. |
| 6,485,413 B1 | 11/2002 | Boppart et al. |
| 6,501,551 B1 | 12/2002 | Tearney et al. |
| 6,552,796 B2 | 4/2003 | Magnin et al. |
| 6,564,087 B1 | 5/2003 | Pitris et al. |
| 6,570,659 B2 | 5/2003 | Schmitt |
| 6,706,004 B2 | 3/2004 | Tearney et al. |
| 6,879,851 B2 | 4/2005 | McNamara et al. |
| 6,891,984 B2 | 5/2005 | Petersen et al. |
| 7,208,333 B2 | 4/2007 | Flanders et al. |
| 7,231,243 B2 | 6/2007 | Tearney et al. |
| 7,241,286 B2 | 7/2007 | Atlas |
| 7,414,779 B2 | 8/2008 | Huber et al. |
| 7,415,049 B2 | 8/2008 | Flanders et al. |
| 7,625,366 B2 | 12/2009 | Atlas |
| 7,801,343 B2 | 9/2010 | Unal et al. |
| 7,813,609 B2 | 10/2010 | Petersen et al. |
| 7,848,791 B2 | 12/2010 | Schmitt et al. |
| 7,916,387 B2 | 3/2011 | Schmitt et al. |
| 7,935,060 B2 | 5/2011 | Schmitt et al. |
| 8,116,605 B2 | 2/2012 | Petersen et al. |
| 8,206,377 B2 | 6/2012 | Petroff |
| 8,325,419 B2 | 12/2012 | Schmitt |
| 8,358,461 B2 | 1/2013 | Huber et al. |
| 8,412,312 B2 | 4/2013 | Judell et al. |
| 8,449,468 B2 | 5/2013 | Petersen et al. |
| 8,478,384 B2 | 7/2013 | Schmitt et al. |
| 8,478,387 B2 | 7/2013 | Xu |
| 8,503,844 B2 | 8/2013 | Petersen et al. |
| 8,581,643 B1 | 11/2013 | Schmitt |
| 8,582,109 B1 | 11/2013 | Schmitt |
| 8,582,619 B2 | 11/2013 | Adler |
| 8,582,934 B2 | 11/2013 | Adler et al. |
| 8,676,299 B2 | 3/2014 | Schmitt et al. |
| 8,687,201 B2 | 4/2014 | Adler |
| 8,753,281 B2 | 6/2014 | Petersen et al. |
| 8,786,336 B1 | 7/2014 | Schmitt |
| 8,831,321 B1 | 9/2014 | Elbasiony |
| 8,902,941 B2 | 12/2014 | Schmitt |
| 8,926,590 B2 | 1/2015 | Petroff |
| 8,948,228 B2 | 2/2015 | Adler |
| 8,948,613 B2 | 2/2015 | Schmitt et al. |
| 8,953,911 B1 | 2/2015 | Xu et al. |
| 9,007,696 B2 | 4/2015 | Petersen et al. |
| 9,069,396 B2 | 6/2015 | Adler et al. |
| 9,091,524 B2 | 7/2015 | Adler et al. |
| 9,138,147 B2 | 9/2015 | Schmitt et al. |
| 9,164,240 B2 | 10/2015 | Schmitt et al. |
| 9,173,591 B2 | 11/2015 | Elbasiony et al. |
| 9,351,698 B2 | 5/2016 | Dascal et al. |
| 9,404,731 B2 | 8/2016 | Adler et al. |
| 9,417,052 B2 | 8/2016 | Adler |
| 9,435,956 B1 | 9/2016 | Ku et al. |
| 9,462,950 B2 | 10/2016 | Xu |
| 9,488,464 B1 | 11/2016 | Schmitt |
| 9,526,424 B2 | 12/2016 | Judell et al. |
| 9,572,495 B2 | 2/2017 | Schmitt et al. |
| 9,610,064 B2 | 4/2017 | Adler et al. |
| 9,702,687 B2 | 7/2017 | Schmitt |
| 9,702,762 B2 | 7/2017 | Friedman et al. |
| 9,833,221 B2 | 12/2017 | Hutchins et al. |
| 9,864,140 B2 | 1/2018 | Adler et al. |
| 9,907,527 B2 | 3/2018 | Dascal et al. |
| 9,940,723 B2 | 4/2018 | Gopinath et al. |
| 9,983,356 B2 | 5/2018 | Schmitt et al. |
| 9,989,945 B2 | 6/2018 | Adler et al. |
| 9,996,921 B2 | 6/2018 | Ambwani et al. |
| 10,006,753 B2 | 6/2018 | Schmitt et al. |
| 10,028,725 B2 | 7/2018 | Petroff |
| 10,089,755 B2 | 10/2018 | Griffin et al. |
| 10,109,058 B2 | 10/2018 | Ambwani et al. |
| 10,140,712 B2 | 11/2018 | Ambwani |
| 10,172,582 B2 | 1/2019 | Dascal et al. |
| 10,222,956 B2 | 3/2019 | Gopinath et al. |
| 10,327,726 B2 | 6/2019 | Dascal et al. |
| 10,331,099 B2 | 6/2019 | Adler et al. |
| 10,335,039 B2 | 7/2019 | Xu |
| 10,338,795 B2 | 7/2019 | Gopinath et al. |
| 10,342,502 B2 | 7/2019 | Dascal et al. |
| 10,453,190 B2 | 10/2019 | Griffin |
| 10,453,196 B2 | 10/2019 | Ambwani |
| 10,499,813 B2 | 12/2019 | Adler |
| 10,529,093 B2 | 1/2020 | Griffin et al. |
| 10,551,251 B2 | 2/2020 | Friedman et al. |
| 10,593,037 B2 | 3/2020 | Gopinath |
| 2002/0161351 A1 | 10/2002 | Samson et al. |
| 2005/0201662 A1 | 9/2005 | Petersen et al. |
| 2006/0095065 A1 | 5/2006 | Tanimura et al. |
| 2009/0174931 A1 | 7/2009 | Huber et al. |
| 2009/0306520 A1 | 12/2009 | Schmitt et al. |
| 2010/0076320 A1 | 3/2010 | Petersen et al. |
| 2011/0157686 A1 | 6/2011 | Huber et al. |
| 2011/0190586 A1 | 8/2011 | Kemp |
| 2012/0075638 A1 | 3/2012 | Rollins |
| 2013/0051728 A1 | 2/2013 | Petroff |
| 2013/0310698 A1 | 11/2013 | Judell et al. |
| 2014/0024931 A1 | 1/2014 | Winston et al. |
| 2014/0094697 A1 | 4/2014 | Petroff et al. |
| 2014/0114182 A1 | 4/2014 | Petersen et al. |
| 2014/0142427 A1 | 5/2014 | Petroff |
| 2014/0142432 A1 | 5/2014 | Hutchins et al. |
| 2014/0142436 A1 | 5/2014 | Hutchins et al. |
| 2014/0187929 A1 | 7/2014 | Schmitt et al. |

(56) References Cited

U.S. PATENT DOCUMENTS

| | | |
|---|---|---|
| 2014/0276011 A1 | 9/2014 | Schmitt et al. |
| 2014/0309526 A1 | 10/2014 | Douk et al. |
| 2014/0379269 A1 | 12/2014 | Schmitt |
| 2015/0119707 A1 | 7/2015 | Schmitt |
| 2015/0297373 A1* | 10/2015 | Schmitt .................... A61F 2/86 623/1.16 |
| 2015/0370229 A1 | 12/2015 | Adler et al. |
| 2016/0022208 A1 | 1/2016 | Gopinath |
| 2016/0058307 A1 | 3/2016 | Svanerudh |
| 2016/0070066 A1 | 3/2016 | Schmitt et al. |
| 2017/0143296 A1 | 5/2017 | Peterson et al. |
| 2017/0188831 A1 | 7/2017 | Adler et al. |
| 2017/0325712 A1 | 11/2017 | Gopinath |
| 2018/0003482 A1 | 1/2018 | Schmitt |
| 2018/0085095 A1 | 3/2018 | Hutchins et al. |
| 2018/0085170 A1 | 3/2018 | Gopinath |
| 2018/0177404 A1 | 6/2018 | Liu |
| 2018/0192957 A1 | 7/2018 | Schmitt et al. |
| 2018/0192983 A1 | 7/2018 | Dascal et al. |
| 2018/0225830 A1 | 8/2018 | Gopinath et al. |
| 2018/0293730 A1 | 10/2018 | Ambwani et al. |
| 2018/0296111 A1 | 10/2018 | Deno et al. |
| 2018/0306569 A1 | 10/2018 | Schmitt et al. |
| 2019/0099237 A1 | 4/2019 | Booker et al. |
| 2019/0365480 A1 | 5/2019 | Gopinath et al. |
| 2019/0220980 A1 | 7/2019 | Ambwani et al. |
| 2019/0307412 A1 | 10/2019 | Dascal et al. |
| 2019/0343409 A1 | 11/2019 | Schmitt |
| 2019/0380594 A1 | 12/2019 | Schmitt et al. |
| 2020/0142575 A1 | 5/2020 | Gopinath et al. |

OTHER PUBLICATIONS

International Search Report and Written Opinion mailed from the International Searching Authority for International Application No. PCT/US2019/034434 dated Oct. 10, 2019 (14 pages).

* cited by examiner

STENT EXPANSION DISPLAY, SYSTEMS, AND METHODS

RELATED APPLICATIONS

This application claims priority to U.S. Provisional Application No. 62/677,623 filed on May 29, 2018, which is incorporated herein by reference in its entirety.

FIELD

The disclosure relates generally to the field of vascular system imaging and data collection systems and methods. In particular, the disclosure relates to methods of evaluating stent expansion levels and presenting related diagnostic information.

BACKGROUND

Coronary artery disease is one of the leading causes of death worldwide. The ability to better diagnose, monitor, and treat coronary artery diseases can be of life saving importance. Intravascular optical coherence tomography (OCT) is a catheter-based imaging modality that uses light to peer into coronary artery walls and generate images thereof for study. Utilizing coherent light, interferometry, and micro-optics, OCT can provide video-rate in-vivo tomography within a diseased vessel with micrometer level resolution. Viewing subsurface structures with high resolution using fiber-optic probes makes OCT especially useful for minimally invasive imaging of internal tissues and organs. This level of detail made possible with OCT allows a user to diagnose as well as monitor the progression of coronary artery disease.

OCT imaging of portions of a patient's body provides a useful diagnostic tool for doctors and others. For example, imaging of coronary arteries by intravascular OCT may reveal the location of a narrowing or stenosis. This information helps cardiologists to choose between an invasive coronary bypass surgery and a less invasive catheter-based procedure such as angioplasty or stent delivery. Although a popular option, stent delivery has its own associated risks.

A stent is a tube-like structure that often is formed from a mesh. It can be inserted into a vessel and expanded to counteract a stenotic condition that constricts blood flow. Stents typically are made of a metal or a polymer scaffold. They can be placed to the site of a stenosis via a catheter. During a cardiovascular procedure, a stent can be delivered to the stenotic site through a catheter via a guide wire, and expanded using a balloon. Typically, the stent is expanded using a preset pressure to enlarge the lumen of a stenosed vessel.

There are several factors that influence the patient outcome when positioning stents. In some procedures, the stent should be expanded to a diameter that corresponds to the diameter of adjacent healthy vessel segments. Stent overexpansion may cause extensive damage to the vessel, making it prone to dissection, disarticulation, and intra-mural hemorrhage. Stent under expansion may inadequately expand the vessel. If the portions of the stent fail to contact the vessel wall, the risk of thrombosis may increase. An under expanded stent may fail to restore normal flow. Proper stent expansion is a difficult problem to address.

There are other challenges associated with stent placements and related procedures. Visualizing a stent placement relative to the wall of a blood vessel using an angiography system is challenging to undertake by inspection. Reviewing images manually to determine stent position on a per image basis is also prone to error.

A need therefore exists for systems, methods, and devices that provide useful diagnostic information related to stent expansion.

The present disclosure addresses these challenges and others.

SUMMARY

In part, the disclosure relates to a method of evaluating stent/scaffold expansion in a blood vessel defining a lumen. In various embodiments, the blood vessels are arteries. The method may include one or more of scanning a stented blood vessel using a first imaging system to obtain a first set of blood vessel image data; storing the first set of blood vessel image data in an electronic memory device in electronic communication with the first imaging system; detecting stent struts along a length of the stented vessel using one more software modules; generating a first representation of a segment of the blood vessel indicative of a level of stent expansion; determining, using the detected stent struts, a first end of the stent and a second end of the stent; defining a first offset distance (D1) from the first end of the stent and a second offset distance from the second end of the stent (D2); generating a second representation of the segment of the blood vessel using D1 and D2 in combination with a tapering profile of the segment; and assessing level of target stent expansion along blood vessel segment by comparing a first value associated with the first representation with a second value associated with the second representation at different positions along the length of the segment.

In one embodiment, scanning the blood vessel is performed using optical coherence tomography, ultrasound, x-ray-base imaging, interferometric imaging, 2D imaging, MRI, 3D imaging, magnetic imaging, or optical imaging. In one embodiment, the blood vessel received one or more stents during a first procedure, wherein the scanning of the stented blood vessel is performed as a diagnostic analysis as an extension of the first procedure.

In one embodiment, the first representation is a first lumen profile of stented blood vessel, wherein the lumen profile is generated based upon actual expansion level of stent along length of the segment. In one embodiment, the second representation is a second lumen profile generated based on a geometric value of blood vessel at each of D1 and D2, wherein the second lumen profile is interpolated based on such geometric values and the tapering profile of the blood vessel.

In one embodiment, the method further includes detecting one or more side branches along the segment, wherein interpolation of the second lumen profile is generated using one or more detected side branches. In one embodiment, the geometric value of blood vessel is selected from the group consisting of an area, a diameter, a chord, a Euclidean distance metric, and a volume.

In one embodiment, wherein assessing level of target stent expansion further includes determining degree of stent expansion relative to a stent expansion threshold using ratio of the first value of first lumen profile to the second value of the second lumen profile at a plurality of positions along the segment.

In one embodiment, the first representation includes one or more views of the blood vessel, wherein one or more views of the blood vessel display detected stent struts and a representation of the lumen of the blood vessel. In one embodiment, the scanning of the stented blood vessel is performed using optical coherence tomography; angiography; ultrasound; x-rays; optical imaging; pressure sensing; flow sensing; and tomographic imaging. In one embodiment, the scanning of the stented blood vessel is performed using an intravascular data collection probe pulled back through the blood vessel. In one embodiment, the scanning of the stented blood vessel is performed using one or more of shadows or reflections from the first set of blood vessel image data.

In one embodiment, D1 and D2 are selected based upon proximity to user selected target landing zones when stent was placed. In one embodiment, the method further includes generating, using one or more computing devices, a blood vessel lumen profile after deployment of a stent in the blood vessel. In one embodiment, the method further includes displaying one or more views of the blood vessel and/or the first vessel representation and displaying one or more visual cues indicating regions of stent under expansion along length of blood vessel segment.

In one embodiment, the method further includes detecting side branches along a length of a segment of blood vessel and displaying side branches relative to lumen. In one embodiment, the side branches are displayed as dots, ellipses, circles, or other shapes relative to the first representation. In one embodiment, the first representation is displayed using user interface of imaging system. In one embodiment, the method further includes scanning the blood vessel with an angiography system and co-registering angiography data with detected stent struts and a first visual cue indicative of stent expansion above a stent expansion threshold and a second visual cue indicative of stent expansion below the stent expansion threshold. In one embodiment, the method further includes visually emphasizing region of first representation that includes stent. In one embodiment, the user interface emphasizes the region by changing contrast, intensity, color of another visual element relative to the region. In one embodiment, D1 and D2 are selected from a distance that ranges from about 0.1 mm to about 1.0 mm. In one embodiment, D1 and D2 are about 0.4 mm.

In part, the disclosure relates to a processor-based system for evaluating a stent expansion in a stented blood vessel. The system includes one or more memory devices; and a computing device in communication with the memory device, wherein the memory device comprises instructions executable by the computing device to cause the computing device to: store a first set of blood vessel image data in an electronic memory device in electronic communication with a first imaging system, the first set of blood vessel image data generated by scanning the blood vessel with the first imaging system; detecting stent struts along a segment of the stented vessel using one more software modules; generate a first representation of a segment of the blood vessel indicative of a level of stent expansion; determine using the detected stent struts, a first end of the stent and a second end of the stent; define a first offset distance (D1) from the first end of the stent and a second offset distance from the second end of the stent (D2); generate a second representation of the segment of the blood vessel using D1 and D2 in combination with tapering profile of the segment; and assess level of target stent expansion along blood vessel segment by comparing a first value associated with the first representation with a second value associated with the second representation at different positions along the segment.

In one embodiment, the first value is a first area or a first diameter, wherein the second value is second area or a second diameter. In one embodiment, the system is a one or a combination of a optical coherence tomography system; angiography system; ultrasound system; x-ray system; CT scan system, optical imaging system; pressure sensing system; flow sensing system; and tomographic imaging system.

The OCT data can be used to generate 2-D views such as cross-sectional and longitudinal views of a blood vessel before or after an initial stent placement or corrective stent related procedure. The OCT data obtained using a data collection probe and various data processing software modules can be used to identify, characterize, and visualize a stent and/or one or more properties relating to the stent and/or the lumen in which it is disposed.

In one embodiment, the one or more outputs are a visual depiction of the target stent profile overlapping one or more regions of the blood vessel lumen profile. In one embodiment, the one or more outputs is a comparative metric of a change in a parameter measured or calculated relative to the segment of the blood vessel. In one embodiment, the parameter is selected from the group consisting of a fractional flow reserve, a flow rate, a vascular resistance ratio, a virtual fractional flow reserve, a simulated fractional flow reserve, a measured fractional flow reserve, and a pressure measurement.

In one embodiment, the method includes generating, using one or more computing devices, a blood vessel lumen profile after placement of a stent in the blood vessel comprises generating a representation of a segment of the blood vessel using a second set of intravascular data obtained with respect to the blood vessel. In one embodiment, the first set of intravascular data is obtained during a first optical coherence tomography imaging session. In one embodiment, the second set of intravascular data is obtained during a second optical coherence tomography imaging session.

One or more devices can display one or more user interfaces and intravascular data or other information derived from such data. The intravascular data can be obtained using IVUS or OCT based data collection systems and probes or other imaging modalities. The methods can be implemented using one or more computing devices and memory storages that receive intravascular data and user inputs via a graphic user interface (GUI) and include one or more image processing and frame selection software components. The computing devices can be microprocessors, ASICs or other processors suitable for use with an intravascular imaging system.

Although, the invention relates to different aspects and embodiments, it is understood that the different aspects and embodiments disclosed herein can be integrated together as a whole or in part, as appropriate. Thus, each embodiment disclosed herein can be incorporated in each of the aspects to varying degrees as appropriate for a given implementation. Further, the various software-based tools to address medical imaging problems and other related challenges and problems and parts of the foregoing can be used for medical applications and other applications for displaying information relating to stents, blood vessels, and two and three-dimensional views thereof without limitation. Other features and advantages of the disclose embodiments will be apparent from the following description and accompanying drawings.

Although, the disclosure relates to different aspects and embodiments and other features as recited and depicted herein, it is understood that the each of the foregoing disclosed herein can be integrated together as a whole or in part, as appropriate. Thus, each embodiment disclosed herein can be incorporated in each of the aspects to varying degrees as appropriate for a given implementation. Further, the various stent expansion diagnostic tools described herein can be used with various imaging modalities.

Other features and advantages of the disclosed embodiments will be apparent from the following description and accompanying drawings.

BRIEF DESCRIPTION OF DRAWINGS

This application contains at least one drawing executed in color. Copies of this patent application publication with color drawings will be provided by the Office upon request and payment of the necessary fee.

The figures are not necessarily to scale, emphasis instead generally being placed upon illustrative principles. The figures are to be considered illustrative in all aspects and are not intended to limit the disclosure, the scope of which is defined only by the claims.

DETAILED DESCRIPTION

In part, the disclosure relates to systems and methods to address the technical problem of detecting stent under expansion and providing diagnostic information to support supplemental stent expansion and balloon selection in the context of blood vessel imaging, analysis and diagnostic systems. As a related challenge of stent placement and proper expansion, reconciling angiography images relative to one or more imaging modalities such that regions of under expanded stents can be easily identified on an expedited timescale is an important technical challenge. The use of co-registration and the generation of various lumen profiles can be used to address this challenge.

If a stent is underinflated it can lead to vessel failure with a year after initial treatment. Accordingly, assessing stent expansion while a patient is in a cath lab immediately after stent placement, generating a representation of stent relative to the artery it is placed in and a corresponding angiography view is a technical solution to the problem of achieving proper stent expansion. The use of models to generate properly/fully expanded lumen models is also described to provide diagnostic guidance regarding stent expansion.

Properly expanding a stent in a blood vessel such as a coronary artery is a significant target outcome because it increases the likelihood of a constricted stenotic region of the artery being successful expanded and kept expanded based on proper balloon selection and stent placement while using imaging modalities to inform the end user. Addressing this technical problem mitigates unfavorable outcomes such as bypass surgery or other procedures.

Figure 1A:
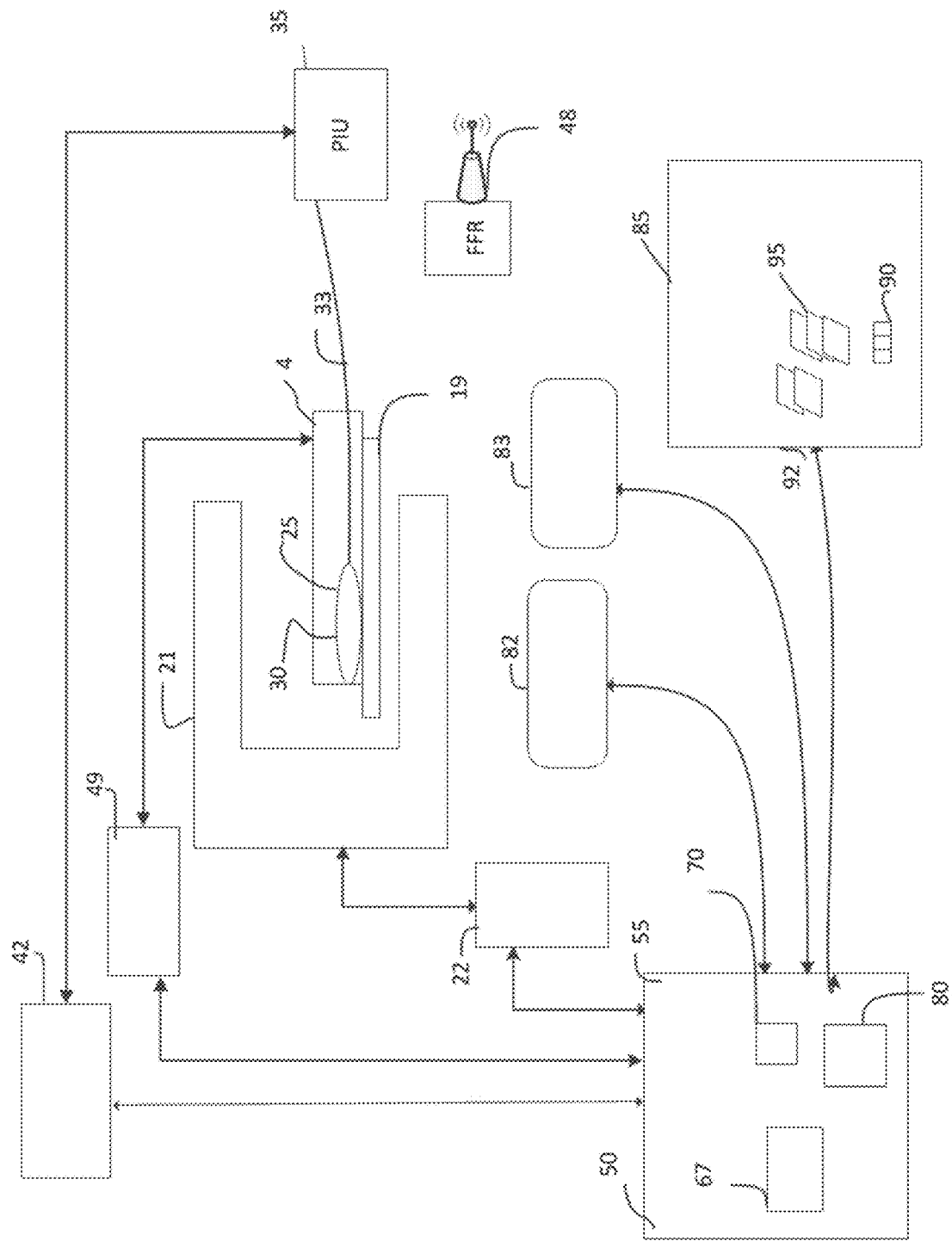
FIG. 1A shows a schematic diagram of an imaging and data collection system suitable for imaging arteries, stents, and other cardiovascular system components in accordance with an illustrative embodiment of the disclosure.

FIG. 1A shows a system 5 which includes various data collection subsystems suitable for collecting data or detecting a feature of or sensing a condition of or otherwise diagnosing a subject 4. In one embodiment, the subject is disposed upon a suitable support 19 such as table bed to chair or other suitable support. Typically, the subject 4 is the human or another animal having a particular region of interest 25.

The data collection system 5 includes a noninvasive imaging system such as a nuclear magnetic resonance, x-ray, computer aided tomography, or other suitable noninvasive imaging technology. As shown as a non-limiting example of such a noninvasive imaging system, an angiography system 21 such as suitable for generating cines is shown. The angiography system 21 can include a fluoroscopy system. Angiography system 20 is configured to noninvasively image the subject 4 such that frames of angiography data, typically in the form of frames of image data, are generated while a pullback procedure is performed using a probe 30 such that a blood vessel in region 25 of subject 4 is imaged using angiography in one or more imaging technologies such as OCT or IVUS, for example.

The angiography system 21 is in communication with an angiography data storage and image management system 22, which can be implemented as a workstation or server in one embodiment. In one embodiment, the data processing relating to the collected angiography signal is performed directly on the detector of the angiography system 21. The images from system 20 are stored and managed by the angiography data storage and image management 22. Other imaging systems disclosed herein can replace or augment system 21.

In part, the disclosure relates to software-based methods, systems and devices suitable for evaluating and depicting information regarding a blood vessel, a stent or other vascular or intravascular information of interest. Various user interface view showing details relating to stent expansion, blood vessel representations, lumen profiles (with partially and fully expanded lumens) relative position of stent endpoints in both angiography and other imaging modalities such as OCT are shown in FIGS. 2A, 2B, 3, 5A, 5B 6A, 6B and 7. In particular, the systems and methods are directed to technical solutions to the technical problem of detecting and mitigating stent underexpansion in general with a particular emphasis on stent expansion using guided imaging/diagnostic systems. Imaging data and data derived therefrom, such as blood vessel representations are generated and displayed as part of a user interface to expeditiously provide diagnostic information. These can take the form of different lumen profiles and ratios of values at corresponding positions along their length such as areas, diameters, or other geometric values.

The system of FIG. 1A includes various components for imaging one or more arteries and/or components of the cardiovascular system using one or more of CT scan, ultrasound, IVUS, X-ray-based imaging modalities, magnetic resonance imaging, optical coherence tomography, infrared, laser-based imaging, and other imaging modalities for intravascular and extravascular imaging. In one embodiment system server 50 or workstation 85 handle the functions of system 22. In one embodiment, the entire system 5 generates electromagnetic radiation, such as x-rays. The system 22 also receives such radiation after passing through the subject 4. In turn, the data processing system 22 uses the signals from the angiography system 21 to image one or more regions of the subject 4 including region 25.

As shown in this particular example, the region of interest 25 is a subset of the vascular or peripherally vascular system such as a particular blood vessel. This subset can be imaged using OCT, ultrasound, alone or combination or one of the other imaging modalities disclosed herein. In one embodiment, this region of interest may include a stent. The stent can be imaged at different points in time such as after deployment and after supplemental stent expansion.

A catheter-based data collection probe 30 is introduced into the subject 4 and is disposed in the lumen of the particular blood vessel, such as for example, a coronary artery. A probe or other device that includes a balloon can also be used to increase the level of stent expansion in response to detecting stent under expansion using one or more imaging modalities.

The probe 30 can be a variety of types of data collection probes such as for example an OCT probe, an FFR probe, an IVUS probe, a probe combining features of two or more of the foregoing, and other probes suitable for imaging within a blood vessel. In one embodiment, a balloon delivery device is moved along guidewire used for the imaging probes disclosed herein. In one embodiment, the probe 30 typically includes a probe tip, one or more radiopaque markers, an optical fiber, and a torque wire. Additionally, the probe tip includes one or more data collecting subsystems such as an optical beam director, an acoustic beam director, a pressure detector sensor, other transducers or detectors, and combinations of the foregoing.

For a probe that includes an optical beam director, the optical fiber 33 is in optical communication with the probe with the beam director. The torque wire defines a bore in which an optical fiber is disposed. In FIG. 1A, the optical fiber 33 is shown without a torque wire surrounding it. In addition, the probe 30 also includes the sheath such as a polymer sheath (not shown) which forms part of a catheter.

The optical fiber 33, which in the context of an OCT system is a portion of the sample arm of an interferometer, is optically coupled to a patient interface unit (PIU) 35 as shown.

The patient interface unit 35 includes a probe connector suitable to receive an end of the probe 30 and be optically coupled thereto. Typically, the data collection probes 30 are disposable. The PIU 35 includes suitable joints and elements based on the type of data collection probe being used. For example a combination OCT and IVUS data collection probe requires an OCT and IVUS PIU. The PIU 35 typically also includes a motor suitable for pulling back the torque wire, sheath, and optical fiber 33 disposed therein as part of the pullback procedure. In addition to being pulled back, the probe tip is also typically rotated by the PIU 35. In this way, a blood vessel of the subject 4 can be imaged longitudinally or via cross-sections. The probe 30 can also be used to measure a particular parameter such as a fractional flow reserve (FFR) or other pressure measurement.

In turn, the PIU 35 is connected to one or more intravascular data collection systems 42. The intravascular data collection system 42 can be an OCT system, an IVUS system, another imaging system, and combinations of the foregoing. For example, the system 42 in the context of probe 30 being an OCT probe can include the sample arm of an interferometer, the reference arm of an interferometer, photodiodes, a control system, and patient interface unit. Similarly, as another example, in the context of an IVUS system, the intravascular data collection system 42 can include ultrasound signal generating and processing circuitry, noise filters, rotatable joint, motors, and interface units. In one embodiment, the data collection system 42 and the angiography system 21 have a shared clock or other timing signals configured to synchronize angiography video frame time stamps and OCT image frame time stamps.

Figure 1B:
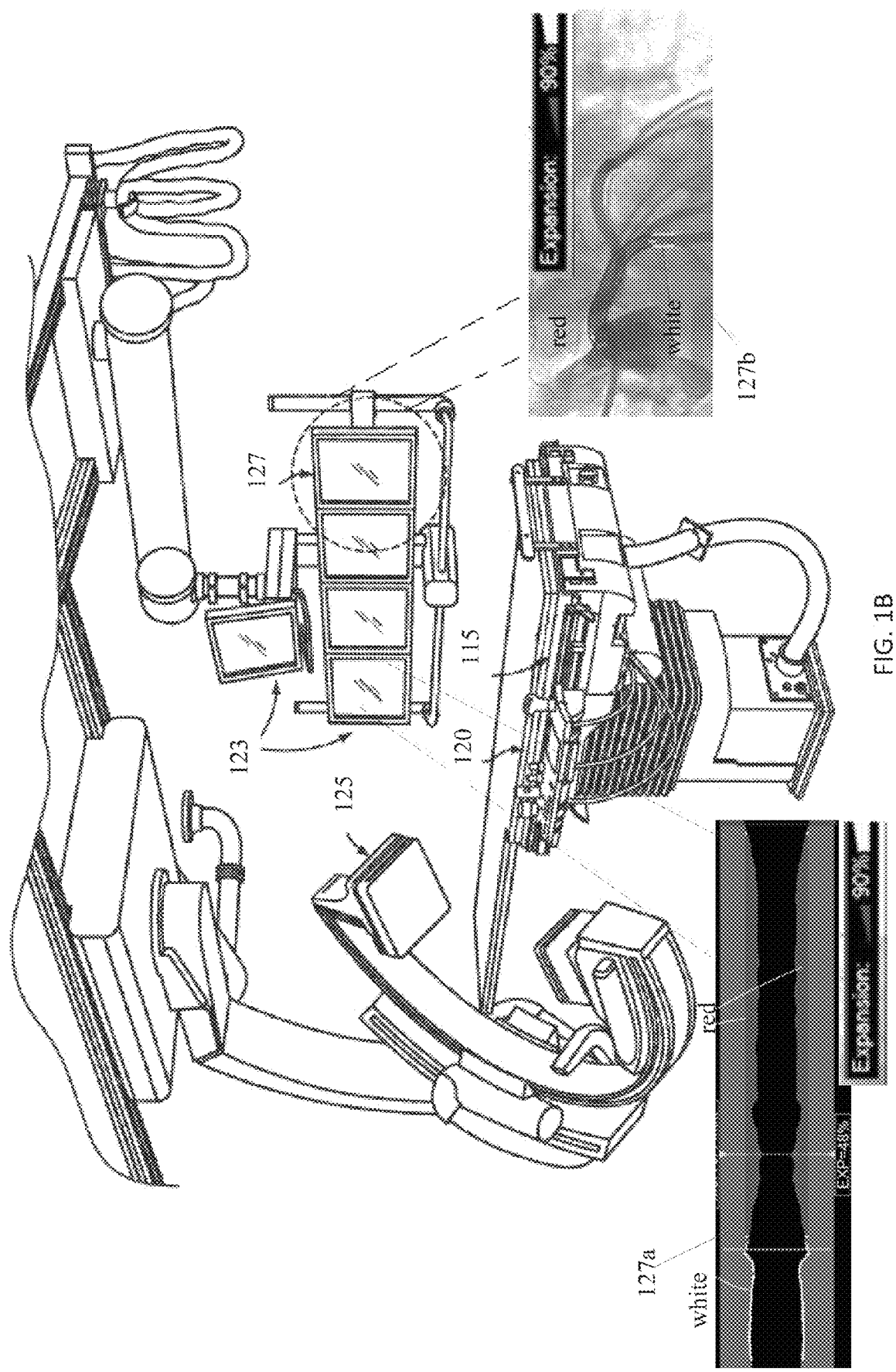
FIG. 1B shows a schematic diagram of an imaging and data collection system suitable for imaging arteries, stents, and other cardiovascular system components that includes multiple displays in accordance with an illustrative embodiment of the disclosure.

Various extravascular imaging systems such as angiography systems can image a given region of interest such as a stent in various states of expansion. The extravascular imaging data can be co-registered with the intravascular imaging data. The outputs of the intravascular and the extravascular imaging modalities can be displayed relative to patient in cath lab using various displays as shown in FIG. 1B.

In addition to the invasive and noninvasive image data collection systems and devices of FIG. 1A, various other types of data can be collected with regard to region 25 of the subject and other parameters of interest of the subject. For example, the data collection probe 30 can include one or more pressure sensors such as for example a pressure wire. A pressure wire can be used without the additions of OCT or ultrasound components. Pressure readings can be obtained along the segments of a blood vessel in region 25 of the subject 4.

Such readings can be relayed either by a wired connection or via a wireless connection. As shown in a fractional flow reserve FFR data collection system, a wireless transceiver 48 is configured to receive pressure readings from the probe 30 and transmit them to a system to generate FFR measurements or more locations along the measured blood vessel. One or more displays 82, 83 can also be used to show an angiography frame of data, an OCT frame, user interfaces for OCT and angiography data and other controls and features of interest.

The intravascular image data such as the frames of intravascular data generated using the data collection probe 30 can be routed to the data collection processing system 42 coupled to the probe via PIU 35. The noninvasive image data generated using angiography system 22 can be transmitted to, stored in, and processed by one or more servers or workstations such as the co-registration server 50 workstation 85. A video frame grabber device 55 such as a computer board configured to capture the angiography image data from system 22 can be used in various embodiments.

In one embodiment, the server 50 includes one or more co-registration software modules 67 that are stored in memory 70 and are executed by processor 80. The server 50 can include other typical components for a processor-based computing server. Alternatively, more databases such as database 90 can be configured to receive image data generated, parameters of the subject, and other information generated, received by or transferred to the database 90 by one or more of the systems devices or components shown in FIG. 1A. Although database 90 is shown connected to server 50 while being stored in memory at workstation 85, this is but one exemplary configuration. For example, the software modules 67 can be running on a processor at workstation 85 and the database 90 can be located in the memory of server 50. The device or system use to run various software modules are provided as examples. In various combinations the hardware and software described herein can be used to obtain frames of image data, process such image data, and register such image data.

As otherwise noted herein, the software modules 67 can include software such as preprocessing software, transforms, matrices, and other software-based components that are used to process image data or respond to patient triggers to facilitate co-registration of different types of image data by other software-based components 67 or to otherwise perform such co-registration. The modules can include lumen detection using a scan line based or image based approach, stent detection using a scan line based or image based approach, indicator generation, stent expansion evaluation and assessment, stent landing zone detection and indication for deployed stents; angiography and intravascular imaging co-registration, and other modules supportive and programmed to perform the methods disclosed herein.

The database 90 can be configured to receive and store angiography image data 92 such as image data generated by angiography system 21 and obtained by the frame grabber 55 server 50. The database 90 can be configured to receive and store OCT image data 95 such as image data generated by OCT system 42 and obtained by the frame grabber 55 server 50.

In addition, the subject 4 can be electrically coupled via one or more electrodes to one more monitors such as, for example, monitor 49. Monitor 49 can include without limitation an electrocardiogram monitor configured to generate data relating to cardiac function and showing various states of the subject such as systole and diastole. Knowing the cardiac phase can be used to assist the tracking of vessel centerlines, as the geometry of the heart, including the coronary arteries, is approximately the same at a certain cardiac phase, even over different cardiac cycles.

The use of arrow heads showing directionality in a given figure or the lack thereof are not intended to limit or require a direction in which information can flow. For a given connector, such as the arrows and lines shown connecting the elements shown in FIG. 1A, for example, information can flow in one or more directions or in only one direction as suitable for a given embodiment. The connections can include various suitable data transmitting connections such as optical, wire, power, wireless, or electrical connections.

One or more software modules can be used to process frames of angiography data received from an angiography system such as system 22 shown in FIG. 1A. Various software modules that can include without limitation software, a component thereof, or one or more steps of a software-based or processor executed method can be used in a given embodiment of the disclosure.

The systems of FIGS. 1A and 1B are suitable for displaying intravascular and extravascular image data. In particular, the systems are advantageous for stent planning and assessment of stent expansion and target stent expansion assessment. In one embodiment, a stent expansion threshold can be provided by the diagnostic system, such as an OCT, IVUS, or other image data collection system, or such a threshold can be adjusted and set by an end user via a user interface. In one embodiment, the stent expansion threshold used to identify regions of stent under inflation range from about 80% to about 90%. Thus, if a stent is inflated at a first location along its length to a level of 48% it is tagged or represented with one visual cue or indicia, while if at another region the stent is expanded to a level at or above the threshold it is identified with another visual cue or indicia.

FIG. 1B shows a cath lab set up with components of an imaging and data collection system, such as system of FIG. 1A for performing OCT, FFR, IVUS, angiography, CT scans or other types of imaging, measurement and assessment for one or more arteries of a patient. A user can interact with the data collection system or otherwise access and display stored image data through the various displays shown. Exemplary user interfaces showing intravascular imaging data and stent expansion data co-registered with angiography data is displayed. A support member 115 such as an accessory rail on a table, bed or other support 120. The support member 115 can be part of the support 120 and a controller can attach directly to the support 120 in one embodiment.

In one embodiment, the controller can include any suitable input device and can be used to navigate user interface screens and parameters such as target stent expansion values and other stent expansion thresholds. In one embodiment, the controller includes an attachment device 60 such as a clamp for mounting as shown. The controller can be used to display and navigate a graphical user interface displayed on one or more monitors or displays 123. In one embodiment, the monitors can be mounted on a ceiling suspension. A graphical user interface 127 can be displayed on a given monitor. Two exemplary graphical user interfaces 127a, 127b are shown in FIG. 1B that include stent expansion and co-registered intravascular data, such as OCT data, and angiography data.

In one embodiment, the controller has a feature set configured to map to commands and menus available to a user as part of the graphic user interface 127. An angiography system or other imaging system disclosed herein 125 can be positioned relative to the support 120 to obtain x-rays of the patient while another data collection procedure such as an OCT procedure is underway. The graphic user interface 127 can display such OCT, angiography, FFR, IVUS, and other data of interest to a user. The controller is configured to control the interface 127 and navigate the menus and image display features it presents to a user. Co-registering the angiography data with intravascular imaging supports assessment of stent expansion levels.

In one embodiment, a healthy lumen profile is effectively simulated using a first geometric value for the distal end of the simulated healthy vessel and a second geometric value for the proximal end of the healthy vessel. In one embodiment, these geometric values are determined at a position offset or shifted relative to a profile of the stented vessel.

These shift or offset values are shown as D1, and D2 in various figures. The geometric values can be cross-sectional areas, diameters, chords, flow values, or other values suitable for interpolating a healthy lumen profile. The simulated healthy lumen profile can then be compared to the stent profile by comparing geometric values of each respective profile in a ratio.

The disclosure describes systems and methods to depict regions of stent under expansion and at a target expansion level relative to a representation of a blood vessel generated using intravascular data to facilitate targeted balloon placement and sizing relative to placed stent. Optical coherence tomography and other imaging modalities can be used to generate various blood vessel representations and to perform various image data processing technique to detect and/or visually represent the lumen L, stent struts SS, side branches SB, and others as shown and described herein.

Figure 2A:
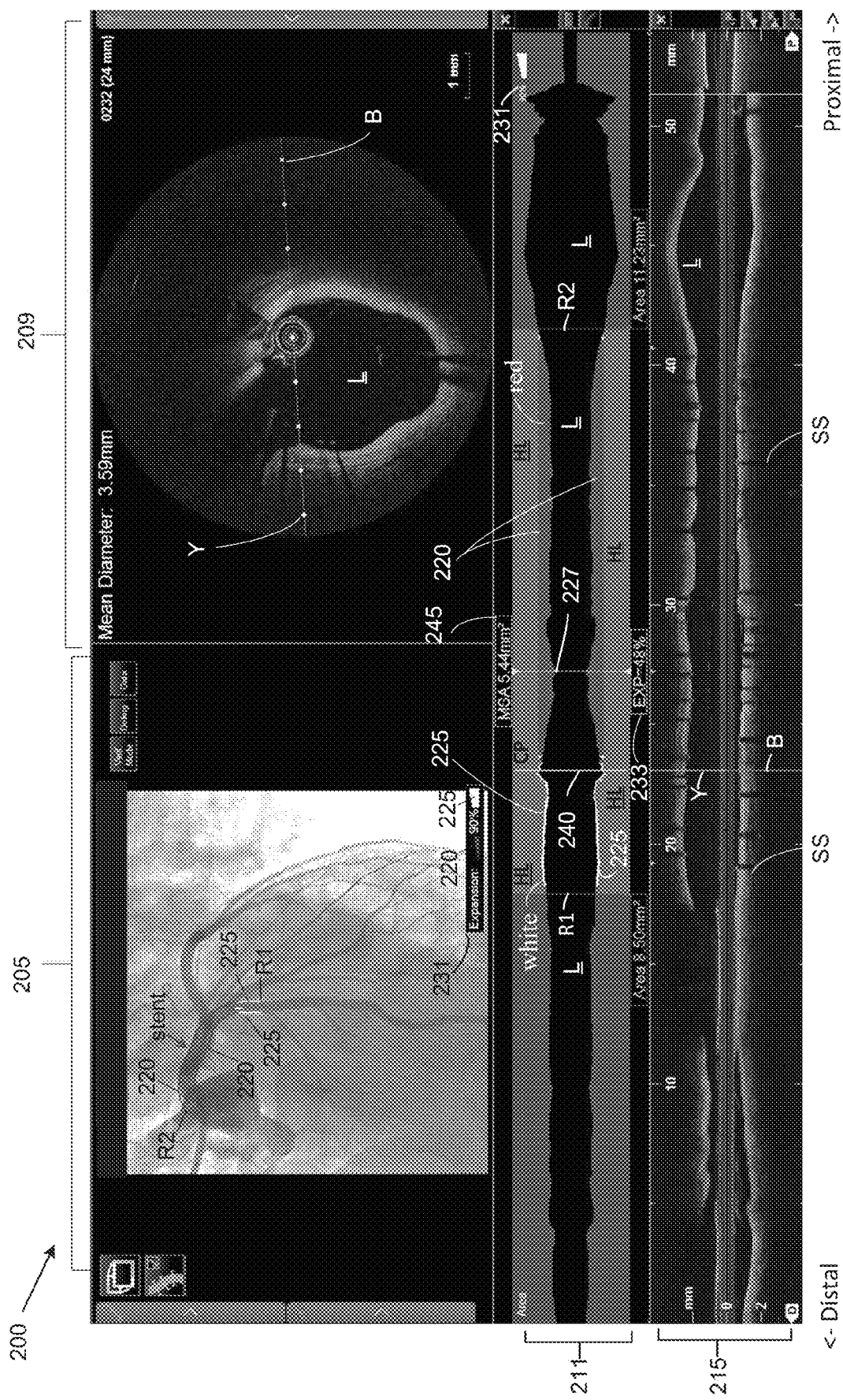
FIG. 2A is a graphic user interface that displays stent expansion analysis results relative to co-registered angiography data, a profile view, and other intravascular imaging views in accordance with an illustrative embodiment of the disclosure.

One or more stent expansion metrics can be used. In one embodiment, the stent expansion metrics can be adjusted by an end user. Thus, a physician can set a stent expansion threshold as a percentage of stent expansion, such as 90% or another percentage. Such a threshold for depicting whether the stent has been expanded to reach this 90% level is shown in FIG. 2A by legend 231 which shows regions along a lumen profile of a stented vessel are underinflated, based on this threshold, red regions, also shown as regions 220. In turn, regions along the length of the stent in which it has been inflated to the 90% or above threshold are shown as white, or as regions 225. A minimum stent area (MSA) in the vessel is also shown by cursor 227 and by MSA in various figures.

If a stent has been detected as under expanded in one or more regions of a blood vessel, as part of a user interface, an indicia 220, such as the color red or another visually cue can be used to show the physician the regions where the stent has been expanded to the target expansion level, 90% in this example, or above that expansion level, regions 225. In this way, the end user can elect to select a balloon based on a suitable diameter to achieve the target expansion level and be able to refer to angiography images and other imaging data to position the selected balloon and increase the expansion of one or more stents in the regions in which they are underinflated.

Figure 5A:
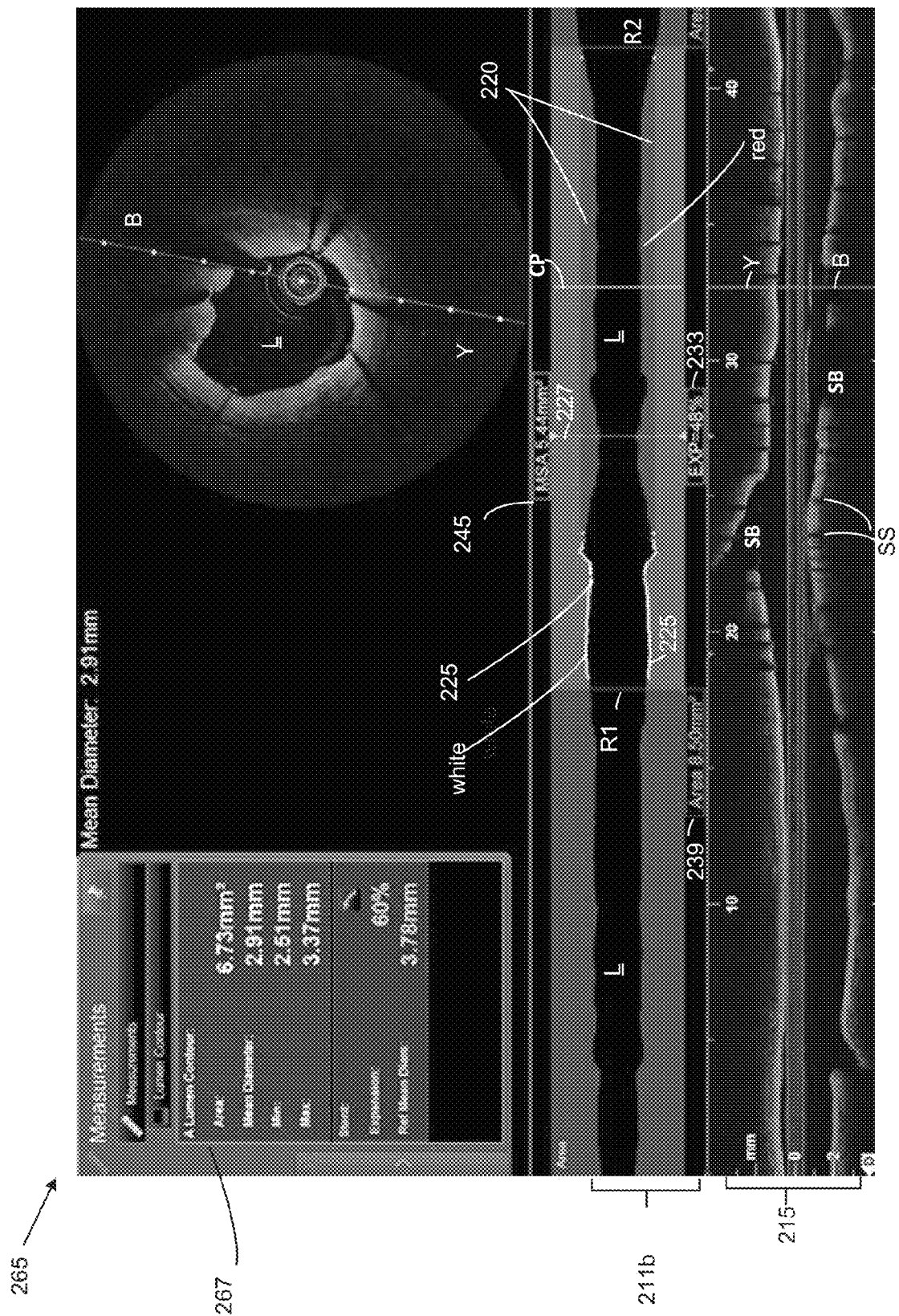
FIG. 5A is a graphic user interface that displays stent expansion analysis results relative to co-registered angiography data, a profile view, arterial measurements, and other intravascular imaging views in accordance with an illustrative embodiment of the disclosure.
Figure 5B:
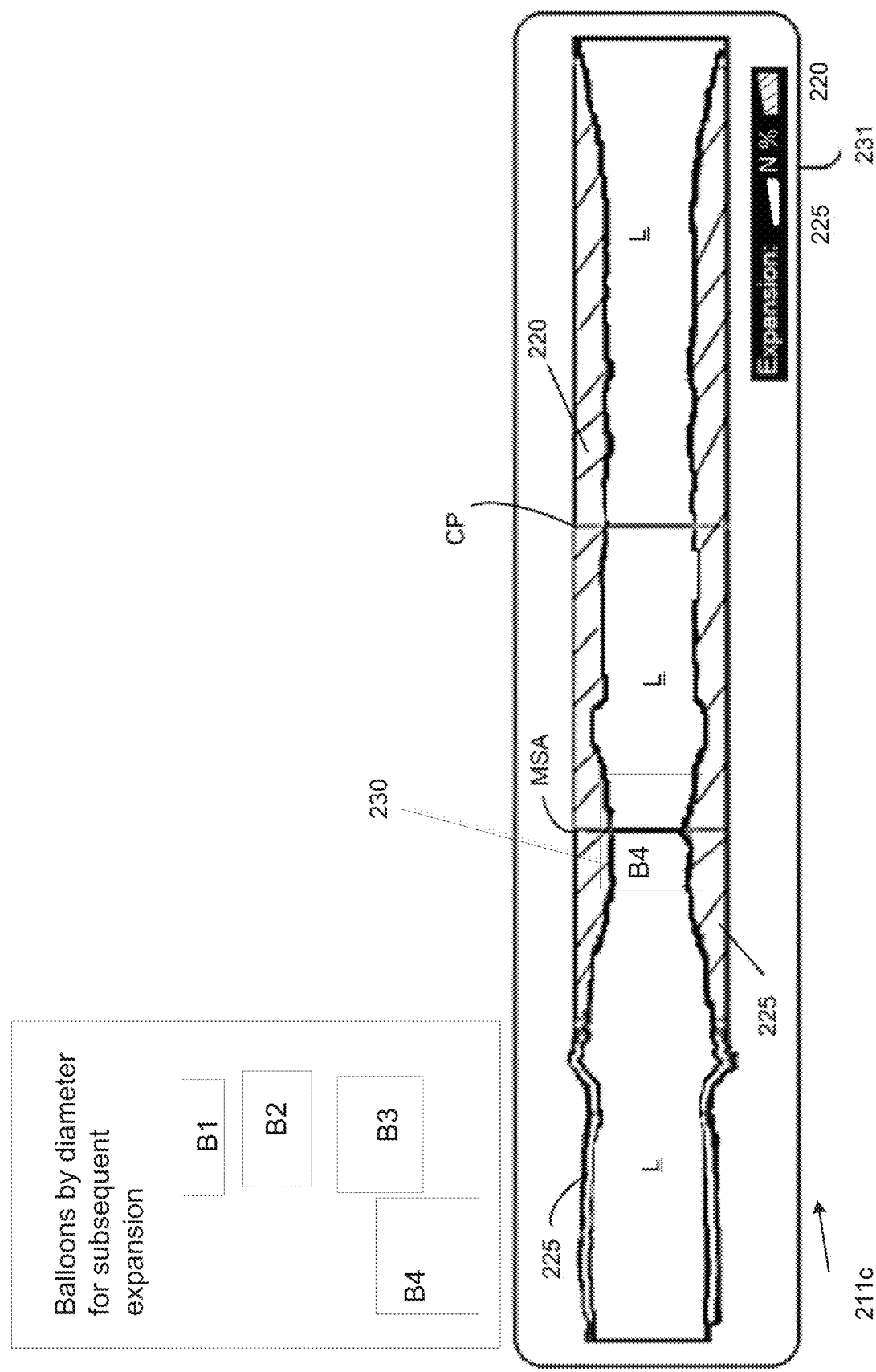
FIG. 5B is a graphic user interface that displays stent expansion analysis results and details relating to balloon sizes suitable for adjusting a stent expansion level in accordance with an illustrative embodiment of the disclosure.

FIG. 5B shows an updated view of a blood vessel representation showing white regions 225 that are above the N % expansion threshold, and hatched regions 220 that are below the N % threshold. A user interface component showing balloons B1, B2, B3, and B4 having various diameters, can be used to overlay them on the figure or measurements can be performed relative to the various representations to select the appropriate balloon diameter. Balloon sizes are offered based on level of stent expansion that is required based on target expansion thresholds or goals. In one embodiment, balloon sizes are calculated based on unexpanded diameter of artery at one or more positions. In one embodiment, the balloons are movable graphical elements that can be user selected and placed relative to a given arterial view depicted herein. An exemplary balloon B4 is shown placed in artery at region 230 that overlaps with the MSA. This region is one location in which expansion is warranted based on stent expansion analysis and thresholds.

Regions of the stent which are shown to be properly expanded, such at the 90% level or above the 90% level, can remain at their current expansion levels while allowing the end user to address regions of under expansion. Selecting the appropriate balloon diameter allows a user to quickly return to the patient, locate the stent and under expanded region on angiography and use the lumen profile views shown herein as a guide to position the balloon in an under expanded region or regions and further expand the stent before concluding the overall session in the cath lab and releasing the patient. Using these various technical diagnostic tools and lumen profiles and expansion ratios, a stent placement that could result in a need for a bypass can be corrected and increase the likelihood of a successful patient outcome.

To further address the problem of properly expanding a stent, co-registration is performed between stent position and expansion levels and angiography systems. FIG. 2A shows an overall user interface that is generated using imaging data from two or more imaging modalities. An angiography image is shown in the angiography interface panel 205 that shows reference locations R1 and R2 which are generated after stent detection is performed on a second imaging modality such as OCT, ultrasound, or others. The regions of stent under expansion 220 are shown in the angiograph view 205 and in the lumen profile view 211. A cross-section of the blood vessel at a cut plan (CP) is shown in interface panel 205. A mean diameter value is shown in this panel as is the lumen L and stent strut shadows. The cut plan is split into two sections labeled as B and Y, which can be color coded as blue and yellow lines.

FIG. 2A shows an exemplary output of diagnostic results to guide an end user after a stent has been placed in a blood vessel. The various diagnostic results are organized in graphical user interface 200. As shown, various panels or regions of the graphical user interface 200 are shown. These include an upper left panel 205 that displays angiography image data that is co-registered with one or more related images or blood vessel representations. The angiography diagnostic interface 205 can also be displayed using an auxiliary display in addition to the common interface display shown in FIG. 2A.

A longitudinal view is shown as part of interface panel 215, which also shows various stent struts SS in the longitudinal view of the imaged vessel. Co-registration has been performed between the angiography image and the lumen profile view 211. The lumen profile view includes a highlighted HL region that is designed to drawn the attention of a user. In this portion of the profile, a cut plane line CP or 240 which corresponds to line segments B and Y together as shown in the other views of the intravascular images shown in panels 209 and 215. The dark lumen L is shown in the middle of the lumen profile view. The stent is coded using a visual cue as shown by regions 220 and 225. These correspond to legend 231, which is used to show the visual cues used for stent under expansion and expansion above the target expansion threshold, shown as 90% in FIG. 2A. The distal direction is on the left and the proximal direction is on the right.

A minimum stent area MSA or 245 is shown and is also tracked using vertical line cursor 227. The MSA is narrowest area of the stent. Further, the regions 220 clearly extend into and show a narrowing relative to the vessel wall representation which bounds the lumen L. In one embodiment, the MSA is identified as a region for balloon deployment to adjust stent expansion after the initial deployment. These regions 220 show where the stent has not been properly expanded to reach the 90% expansion threshold. Regions 225, which are shown to the left of cut plane 240 are expanded at or above the 90% threshold. These representations allow an end user to go back to the patient and place a balloon on a delivery catheter while a guidewire is still in the blood vessel and position the balloon using live angiography and reference the views shown in FIG. 2B to properly place a balloon of the correct diameter to inflate target areas 225. These various tools solve the complex technical problem of properly expanding a stent. This process reduces the overall time a patient spends in the cath lab by expediting a subsequent stent expansion, should regions requiring it exist.

These systems, devices, and methods are implemented when a subject is first evaluated using a diagnostic method such as one or more cardiac imaging modalities. These imagining modalities can include, without limitation, OCT, IVUS, computer aided tomography, MRI, angiography, x-rays, pressure data-based models of heart and/or blood vessel operation and status.

In part, the disclosure relates to systems, methods and devices to evaluate a placed stent in a blood vessel relative to one or more planning stages and profiles obtained with respect to the blood vessel or stent. The profiles and information relating to the blood vessel or stent can be obtained using an intravascular data collection system and related probes, such as an optical coherence tomography (OCT) or intravascular ultrasound (IVUS) or other intravascular data collection modalities. Further, the disclosure provides an automated method for a user, such as a clinician or other person, to evaluate whether a stent placed in a blood vessel has been expanded to a suitable level such as a substantially optimal level or other suitability metrics. These metrics can be user specified in one embodiment.

Figure 6A:
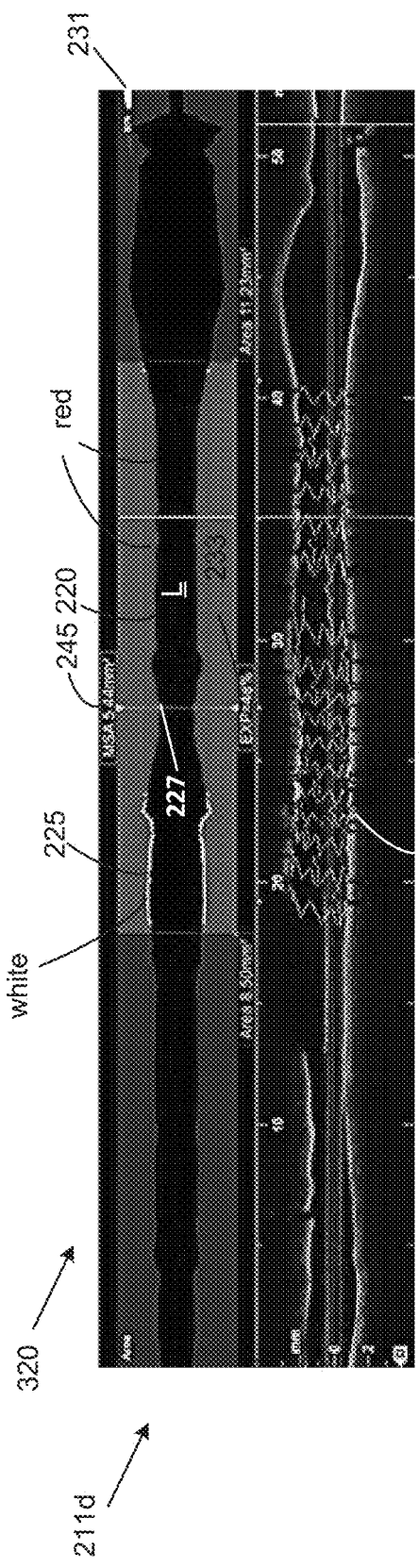
FIGS. 6A and 6B are graphic user interfaces that display stent expansion analysis results relative to a profile view and detected stent struts in another arterial view in accordance with an illustrative embodiment of the disclosure.
Figure 6B:
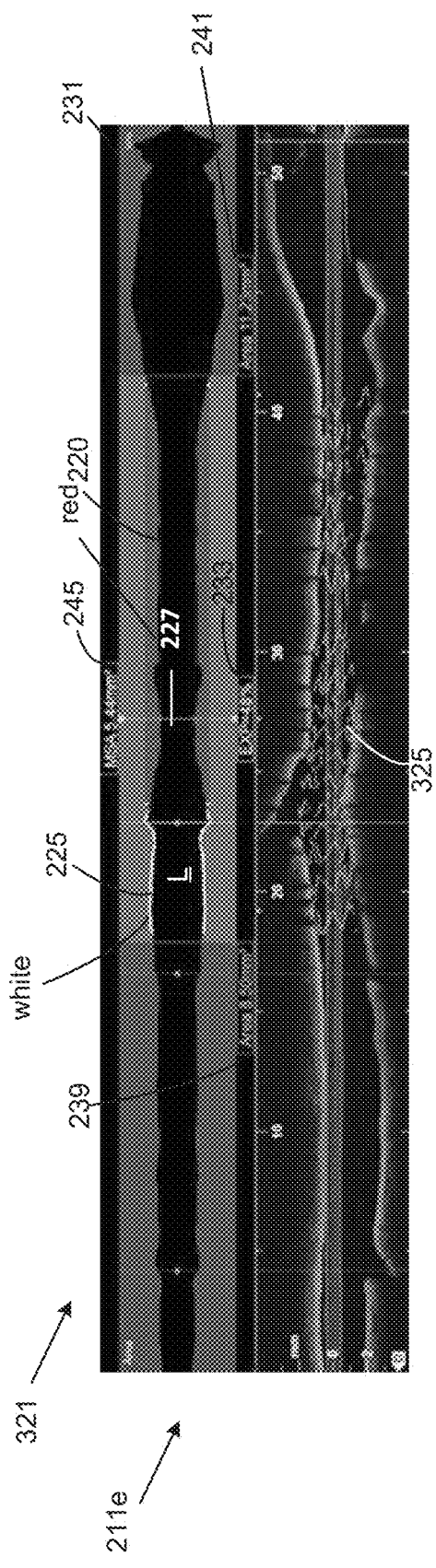

In part, the disclosure relates to a method of evaluating stent placement in a blood vessel. The method includes generating, using one or more computing devices, a representation of a segment of the blood vessel using a first set of intravascular data obtained with respect to the blood vessel, wherein a stent has been positioned in the blood vessel. This is shown in the various lumen profile views 211, 211b, 211c, 211d, 211e, (see FIGS. 2A, 2B, 5A, 5B, 6A, and 6B) in which a stent is displayed and regions of proper expansion relative to a N % expansion threshold and under inflation are shown. FIGS. 6A and 6B show user interfaces 320, 321 that include detected stent struts 325 in the bottom panel and lumen profile views 211d and 221e that show MSA, EXP, and regions of expansion about 90% threshold (See legend 231). Regions 220 that would benefit from further expansion are shown in each respective lumen profile view. These figures can also be co-registered with an angiography system.

Figure 8:
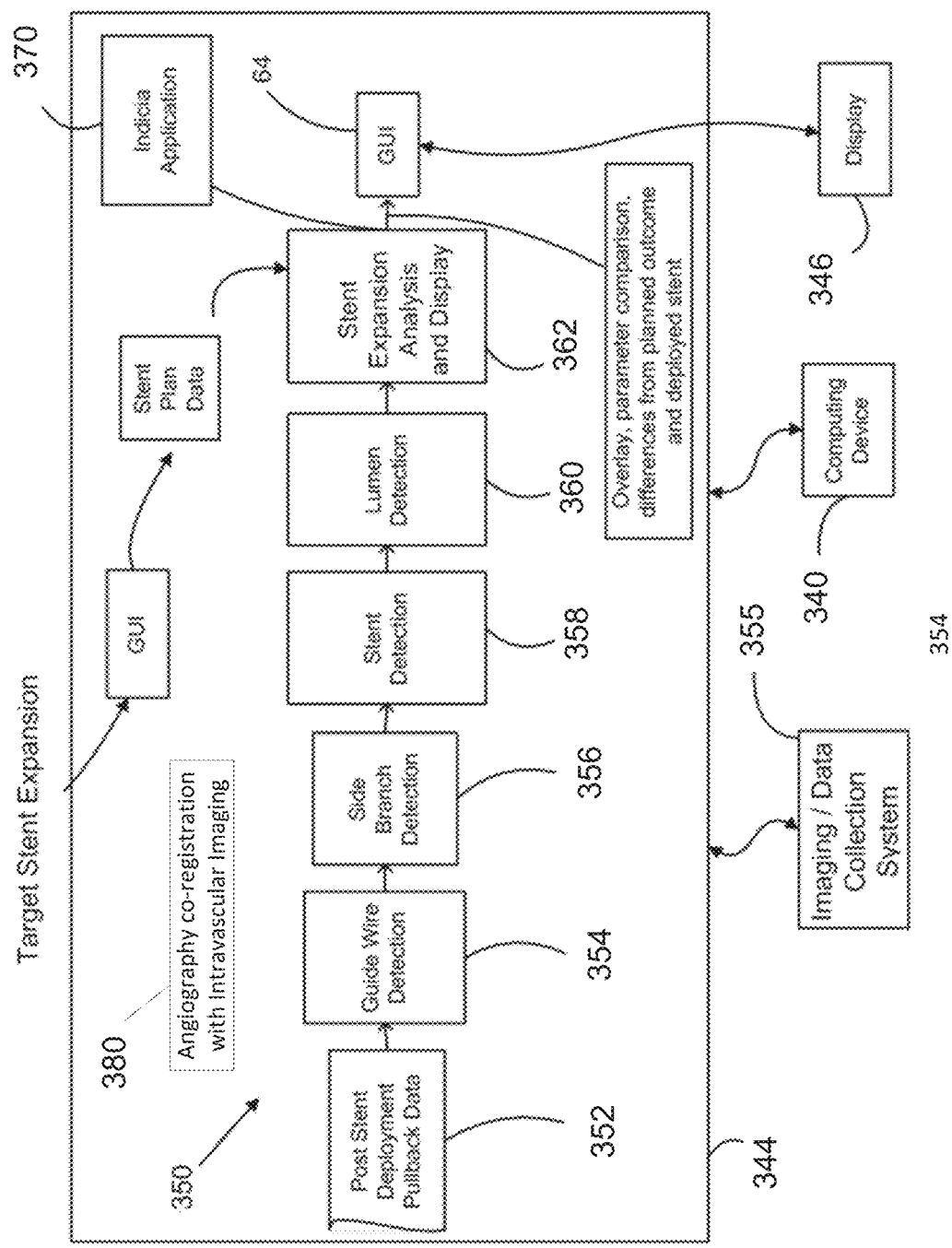
FIG. 8 is a schematic diagram of a software-based image processing pipeline suitable for analyzing stent expansion and other artery-related parameters in accordance with an illustrative embodiment of the disclosure.

As part of the overall system and method, various imaging processing techniques are performed using systems, such as the systems disclosed herein, including with regard to FIGS. 1A, 1B, and 8. The image processing steps can include lumen boundary detection, which corresponds to boundary between lumen L and wall of blood vessel which bounds it, stent detection, side branch detection, and others. Lumen detection informs stent detection because it gives a location relative to which stents are going to exist in the image.

The lumen detection software can include one or more steps. For example, to perform lumen detection in one embodiment a filter or other image processing device can be applied to a two dimensional image to detect edges in the images, the edges indicative a lumen boundary. In another embodiment, a scan line based approach is used. During one or more pullbacks, optical or ultrasound signals are collected as scan lines with respect to a blood vessel and one or more stents disposed in the lumen of the vessel. In one embodiment, the lumen detection software executing a computing device generates one or more images from the set of scan lines using a computing device. Lumen detection can also be performed using other image data sets from other imaging systems.

Once stent struts have been detected, they can be displayed in the various images as shown. After stent detection, and as part of the generation of a lumen profile view, an offset distance D1 and D2 are generated. These can be a shift in distance to the left and right (proximal and distal) or vice versus. In FIG. 2A, these references are shown by lines R1 and R2.

Figure 2B:
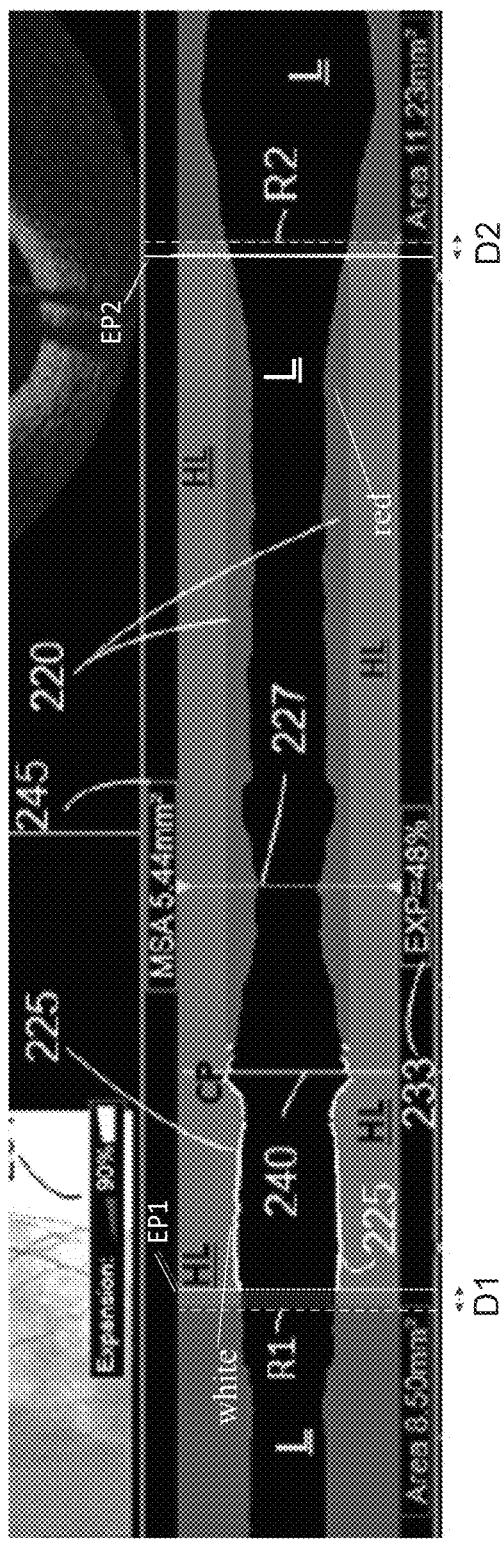
FIG. 2B is a graphic user interface that displays stent expansion analysis results relative to a profile view in accordance with an illustrative embodiment of the disclosure.

In FIG. 2B, R1 and R2 are shown as dotted lines. The end points of the stent are shown by vertical lines EP1 and EP2, these are first and second endpoints of the stent. These can be detected automatically once stent detection software module has detected the stents. The stent endpoints are used to generate the references R1 and R2, which are lines that are automatically generated a distance away from the lumen. These distances are D1 and D2 as shown by double headed arrows in FIG. 2B. The area of the lumen at these offset distances is also shown. The more distal area at offset distance D1 is shown as 8.5 mm2 and the larger more proximal area for the other offset distance D2 is shown as 11.23 mm2. The length of D1 and D2 are typically equal but can vary. They are usually a relatively short distance from the stent endpoint and range from about 0.1 mm to about 1 mm. A value such about 0.4 mm or about 0.5 mm is desirable but other off set distances can be chosen. The first reference R1 may be the distal reference and the second reference R2 may be the proximal reference and vice versa.

Figure 7:
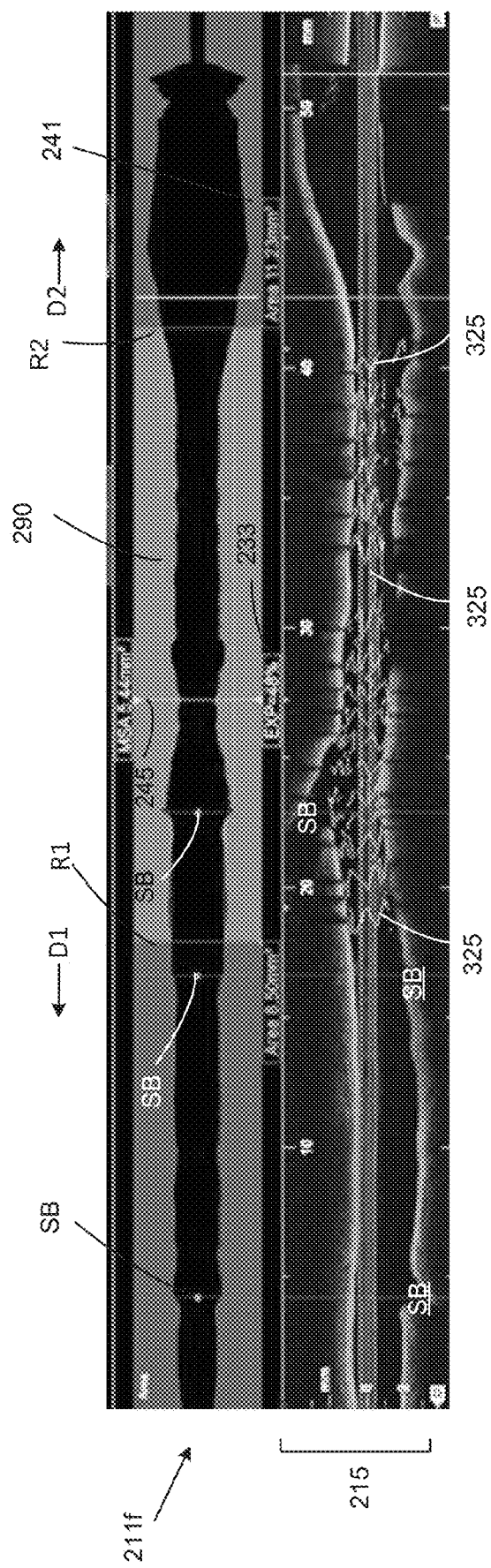
FIG. 7 is a graphic user interface that displays stent expansion analysis results relative to a profile view and detected stent struts in another arterial view in accordance with an illustrative embodiment of the disclosure.

The offset distances D1 and D2 are used to move a distance away from the stent endpoints because the lumen area, distance or other geometric values at these points are used to generate another lumen profile that has a tapering profile 290 such as that shown in as 211a (see FIG. 3) and 211f (see FIG. 7). Stent placement can be considered a proxy for healthy regions of the blood vessel. Selecting stent endpoints themselves can have various errors do to the viewing plane, output of the stent detection software module, and reflections from the stent strut at the end point, blooming effects, and others.

As a result, selecting a position offset from the stent endpoint, D1 and D2, allows a geometric value of the lumen profile, such as the area or diameter of the lumen to be selected at two points. These values can be used to interpolate a tapering profile 290 which can be used as fully expanded lumen profile. Thus, by interpolating such a lumen profile 290, which corresponds to the outcome if a stent were not needed and there was no stenosis in between reference R1 and R2, a lumen profile can be generated using image data processing software. The lumen profile that corresponds to a fully expanded lumen that spans the same region as the stent, allows for the expansion ratio to be calculated at each position along the stented region.

Figure 3:
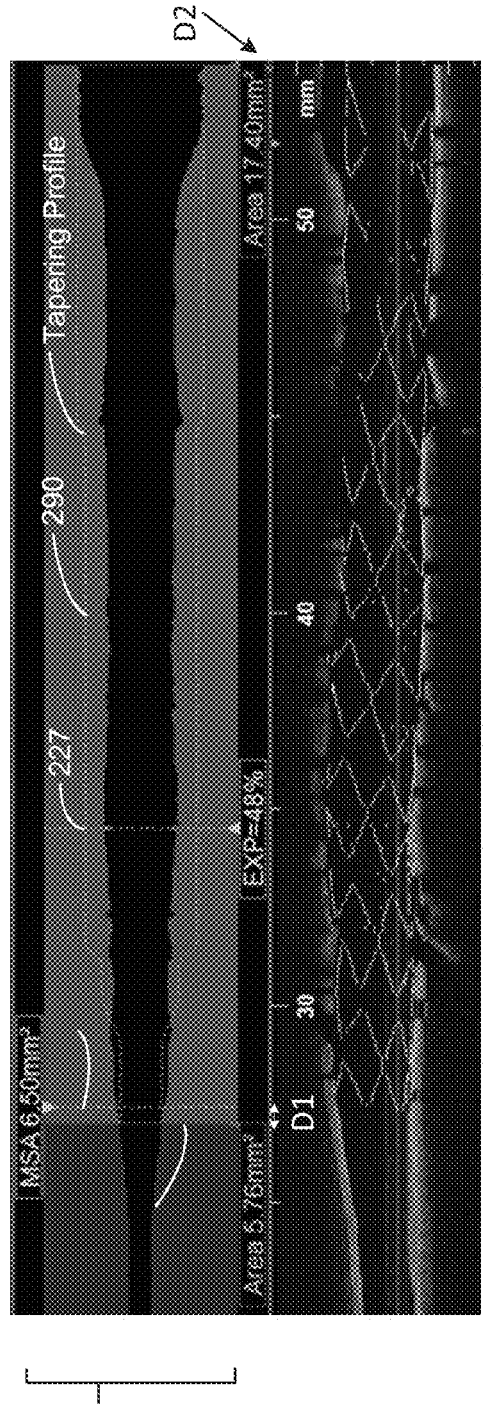
FIG. 3 is a graphic user interface that displays stent expansion analysis results relative to a profile view and detected stent struts in another arterial view in accordance with an illustrative embodiment of the disclosure.

Specifically, the ratio of a cross sectional area or a diameter or another value from the stented lumen profile can be compared to the corresponding cross sectional area or a diameter or another value from the interpolated, full expanded lumen profile, to generate the N % stent expansion threshold. In FIG. 7, for example, the dotted tapering profile shows what a fully expanded lumen would look like if the tissue was stenosis free. This can be compared to the area or diameter values obtained from the lumen profile generated after stent detection to shown the amount of expansion at different points. In one embodiment, the minimum expansion frame 48% (EXP) is also called out automatically as shown in FIGS. 2B, 3, and 7. This frame indicates where the stent is least expanded. As a result, this can serve as target for further expansion with a balloon. The co-registration with angiography can further help guide such a balloon placement.

In one embodiment, the method includes generating and displaying a expansion levels based on the N % expansion ratio obtained using a first representation of the blood vessel (stent expansion-based) and an interpolated expanded second representation that is generated without a stent being present. Simulating a healthy lumen profile representation facilitates generating a metric to assess stent expansion levels and to show when this metric is satisfied (expanded above N %) or not (not expanded enough at position X to reach N % expansion). These representations can be obtained using intravascular data or other imaging data. The foregoing steps are performed such that the representation is coregistered with one or more angiography images of the blood vessel. Given this diagnostic representation of the imaging data, a user can then place the stent in the stenotic regions identified as targets for stent placement.

Further, after one or more stents have been placed in the artery, a second imaging session is performed such as a second intravascular pullback performed during angiography. A second representation of the artery can be generated and the one or more stents that were repositioned or expanded can be assessed.

In part, the disclosure relates to a processor-based stent placement evaluator or evaluation system. The system or evaluator includes one or more memory devices; and a computing device in communication with the memory device, wherein the memory device comprises instructions executable by the computing device to cause the computing device to generate one or more representations of a vessel after performing stent detection such that the level of stent expansion achieved relative to a threshold or other metric can be displayed with suitable indicia or graphic user interface elements to quickly present information to the end user to reduce the time a subject spends in the cath lab. A user can measure the vessel and various parameters using the interface features shown, such as in FIG. 5A. Further, once the diagnostic information is available to the end user, they can select a proper balloon based on requisite diameter to further expand the stent and thereby increase blood flow in the stenotic regions and avoid follow on procedures.

In FIG. 5A, various user interface panels are shown. Various measurements determined from the use of various software modules and operations from software pipeline in FIG. 8 can be determined and displayed as shown in measurement interface panel 267. For a given lumen contour, an area, a mean diameter, a radius, a minimum diameter, and a max diameter can be determined and displayed. Various regions of a detected stent are shown in highlighted region of middle profile view 211b in which lumen L and R1 and R2 are labeled. In one embodiment, regions along the length of the stent in which it has been inflated to the 90% or above threshold are shown as white, or as regions 225. A minimum stent area (MSA) in the vessel is also shown by cursor 227 and by MSA in various figures. The expansion of stent at the MSA is shown as about 48%. References to white and red in the figures are but one example of a distinguishing color or indicia. Other indicia can be used in a given embodiment.

If a stent has been detected as under expanded in one or more regions of a blood vessel, as part of a user interface, an indicia 220, such as the color red or another visually cue can be used to show the physician the regions where the stent has been expanded to the target expansion level, 90% in this example, or above that expansion level, regions 225.

In part, the disclosure relates to operations and methods performed upon diagnostic data such as intravascular data generated using a diagnostic system. Examples of such a system can include an optical coherence tomography, an intravascular ultrasound imaging and other data intravascular data collection systems. The methods and systems described herein can use various steps and processing stages to perform one or more imaging pullbacks to collect intravascular data. Each or a subset of the one or more pullback imaging sessions can also be imaged in parallel using an angiography system The disclosure relates to various methods, systems, and apparatus relating to stent detection and stent representations as part of diagnostic and procedural information systems suitable for assisting with stent planning. In part, the disclosure includes embodiments and features described in the patent application entitled "STENT AND VESSEL VISUALIZATION AND DIAGNOSTIC SYSTEMS, DEVICES, AND METHODS" filed on Jul. 24, 2015 and having U.S. Patent Application Pub. No. 20160022208 and the patent application entitled "METHOD AND APPARATUS FOR AUTOMATED DETERMINATION OF A LUMEN CONTOUR OF A STENTED BLOOD VESSEL" filed on Mar. 12, 2013 and having U.S. Patent Application Pub. No. 20150297373, the entire disclosure of each of which is incorporated herein by reference.

In part, the disclosure relates to computer-based methods, devices, and systems suitable for imaging a blood vessel using one or more imaging modalities, co-registering the imaging modalities, and representing the imaged blood vessel with detected stents shown relative thereto. Levels of stent under expansion and expansion within predetermined target expansion levels are also shown. Various systems and imaging modalities can be used to solve the problem of how to properly expand a stent as disclosed herein. Additional details relating to an exemplary system are discussed herein including with regard to FIGS. 1A and 1B. It is informative to describe the outputs of the system which are used to provide the diagnostic guidance to address the technical challenges of stent expansion.

A two-dimensional view of the blood vessel having the lumen L labelled is shown in graphic user interface panel 209. The line segments labeled as B or Y correspond to the segments in the bottom panel 215. A lumen profile panel 211 is shown in the middle of the overall interface 200. The lumen profile view has two central reference frames R1 and R2 which bound the section of the blood vessel in which a stent has been detected and displayed in the representation shown.

FIG. 2B shows a zoomed in view of lumen profile 211 graphical user interface with the endpoints of the stent shown by the vertical dotted lines EP1 and EP2. These endpoints of the stent are determined using the detected stent struts that span a subset of a segment of the blood vessel.

In one embodiment an offset distance is used to shift away from the edge of first stent strut detected in a frame of image data and the edge of the last stent strut detected in a frame of image data. The tapering profile interpolated using a first reference frame and a second reference frame can be incorrectly modeled if the end stent strut throws off the geometric value that should be used to model a healthy lumen profile. Accordingly, a shift distant, offset or a position along the blood vessel representation is selected that moves a distance away from the ends of the stent. These distances are shown as D1 and D2 in FIG. 2B. These can be used to generate the lumen profile 211a that shows a tapering profile 290 that can be used as the basis for comparing to the stented lumen profiles described and depicted herein.

When placing a stent, it is advantageous to select landing zones that are normal/healthy tissue, this facilitates the interpolation of simulation of a healthy fully expanded vessel as a baseline comparator for the lumen profile that arises based on how the stent was actually expanded/under expanded. In one embodiment, cursors or other on-screen user interface elements are placed at both ends of a stented region, such as reference points R1 and R2. The cross-sectional area or another blood vessel parameter is automatically displayed with regard to each end of the stented region. The D1 and D2 offsets can be computed by shifting away from the stent endpoints at R1, R2/EP1, EP2.

Figure 4A:
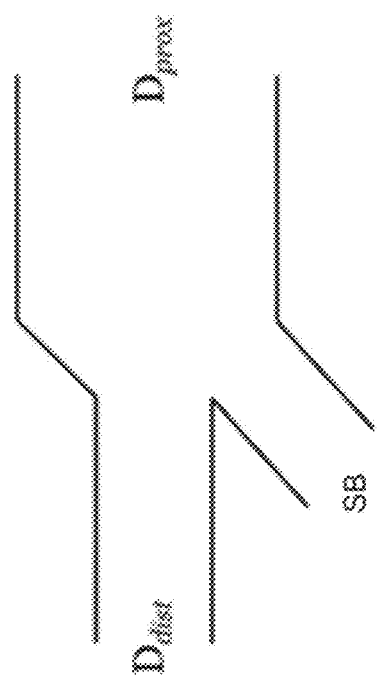
FIGS. 4A and 4B are schematic representation of blood vessels that include one or more side branches as shown that are suitable for generating a lumen profile model suitable for analyzing stent expansion in accordance with an illustrative embodiment of the disclosure.
Figure 4B:
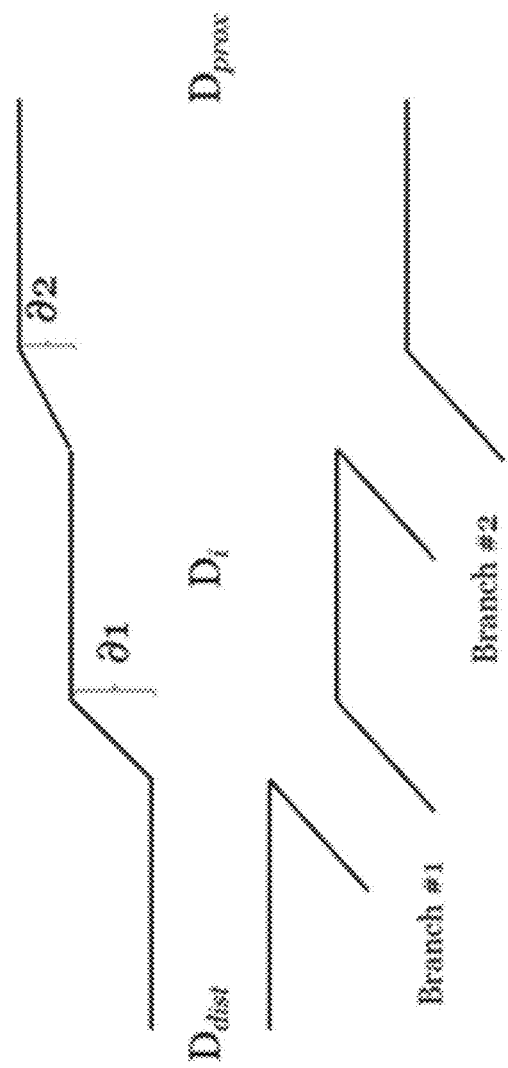

FIGS. 4A and 4B show schematic representation of blood vessels that include one or more side branches as shown that are suitable for generating a lumen profile model/representation of a healthy version of an imaged blood vessel for comparison to the recently stented and imaged blood vessel. Various methods can be used to interpolate a tapering profile to generate a basis for comparison to the actual levels of stent expansion performed and measured after stent detection is complete.

The blood vessels being imaged, such as coronary arteries, taper from proximal to distal and the size of the side branches in between influence the amount of taper. As part of the tapering, when moving from proximal to distal, blood vessel diameter decreases. The step down in diameter when traversing a side branch is directly proportional to the diameter of the intermediate side branch. FIG. 4A shows the tapering due to an intermediate side branch SB, where $D_{prox}$ is the diameter of the proximal vessel and $D_{dist}$ is the diameter of the distal reference, B is the diameter of the intermediate side branch and the scaling exponent (exp) ranges over various values as per the models and related equations disclosed herein and as disclosed herein.

A vessel tapering profile or relationship for a single side branch can be used compute the ideal taper in a stented segment using the distal and proximal reference frames and multiple intermediate side branches. As shown, in FIG. 4B, the tapering from proximal to distal segment is shown along with two intermediate side branches. The increments $\partial_1$ and $\partial_2$ can be computed using a vessel scaling law to provide a continuous tapered reference from the proximal to distal segment.

If there are multiple intermediate side branches as shown in FIG. 4B, the increment due to each side branch needs to be computed and the intermediate reference diameter $D_1$ may be calculated. The intermediate reference diameter will then allow for a continuous estimate of the taper from the proximal to the distal reference segment. Other interpolation techniques can also be used to generate a tapering profile. In one embodiment, the follow relationships are used.

$$D_{prox}^{\frac{7}{3}} = D_{dist}^{\frac{7}{3}} + B^{\frac{7}{3}} \qquad \text{eq. 1}$$

$$D_i = D_{dist} + \partial_1 \qquad \text{eq. 2}$$

$$D_{prox} = D_{dist} + \partial_1 + \partial_2 \qquad \text{eq. 3}$$

The side branch location and diameter can be measured while the distal and proximal reference frames diameters are known. The individual increments $\partial_1$ and $\partial_2$ are unknown need to be computed. A generalized approach to estimating the increments that can be used for any number of intermediate side branches is shown below:

The difference between the proximal and distal reference diameter is:

$$\Delta = D_{prox}^{exp} - D_{dist}^{exp} \qquad \text{eq. 4}$$

$d_{prox}$ is the diameter of the proximal reference frame and $d_{dist}$ is the distal reference frame diameter.

$$\Delta = \Sigma_i^N \partial_i \qquad \text{eq. 5}$$

$\partial_1$ is the increment or step up from the distal to proximal reference at the $i^{th}$ branch, with N total branches. Segment increment at each branch is directly proportional to the diameter of the branch B raised to the scaling law exponent.

$$\partial_i \propto B_i^{exp} \qquad \text{eq. 6}$$

The contribution of the $i^{th}$ branch to the increment $\partial_i$ in the $i^{th}$ segment is:

$$\partial_i = \frac{B_i^{exp} * \Delta}{\Sigma_i^N B_i^{exp}} \qquad \text{eq. 7}$$

Diameter of reference profile in segment i is computed as:

$$D_i = \sqrt[exp]{D_{i-1}^{exp} + \partial_i} \qquad \text{eq. 8}$$

In various embodiments, tapered reference profile/tapering profile 290 is shown on the lumen profile, such as in FIGS. 3 and 7. The increments in the taper occur at each automatically detected side branch as shown on the lumen profile. The proximal and distal frames are automatically located using the stent detection features. FIG. 3 also shows the location of the minimum expansion frame (EXP) and the expansion percentage at that frame and the MSA frame.

The adaptive ideal reference profile is computed using the natural taper of the vessel due to side branches. There is a mathematical relationship between the distal and proximal reference and the intermediate side branch of equation 1.

$$D_{prox}^{\frac{7}{3}} = D_{dist}^{\frac{7}{3}} + B^{\frac{7}{3}} \qquad \text{eq. (1)}$$

Where $D_{prox}$ is the diameter of the proximal vessel and $D_{dist}$ is the diameter of the distal reference, B is the diameter of the intermediate side branch. In case no major side-branch is detected between the distal and the proximal reference, the ideal lumen diameter at each location is calculated by using linear interpolation between the distal and the proximal references.

In cases of multiple side branches, the ideal reference profile between the distal and proximal reference frames is tapered with a step at each side branch, the larger side branch contributes proportionally to a larger step. This can be seen in the dotted line of the tapering profile 290.

If the distal and proximal reference frames are in the same segment, the stent profile is a linear interpolation between the distal and proximal reference fames. In one embodiment, the method to determine a target stent profile in response to one or more user selected reference frames is as follows. Determining the total number of side branches between the reference frames is input as N.

For example if four (N=4) side branches are shown between the most distal and proximal frame of the segment shown. Side branches are shown in figures as SB or as circle or dots as visual cues, such as in FIG. 1A side branch is at the top of the lumen and three are disposed at the bottom. exp=2.3 is the scaling exponent. In one embodiment, the exp values ranges from greater than or equal to about 2 to less than or equal to about 3. This exp value describes scaling of the taper of the segment between the user selected reference frames. In normal subjects the exp value ranges from about 2.2 to about 2.7. In one embodiment, the exp value is about 7/3 or about 2.333. In other embodiments, exp is less than about 3.

The difference between the proximal and distal reference diameter is:

$$\Delta = d_{prox}^{exp} - d_{dist}^{exp}$$

$d_{prox}$ is the diameter of the proximal reference frame and $d_{dist}$ is the distal reference frame diameter.

$$\Delta = \sum_{n}^{N} \partial_n$$

$\partial_n$ is the increment of stent segment at the nth branch (to be calculated)
Segment increment at each branch is proportional to the diameter of the branch raised to the scaling law exponent.

$$\partial_n \propto BranchD_n^{exp}$$
$$\partial_n = \frac{Branchd_n^{exp} * \Delta}{\sum_n^N BranchD_n^{exp}}$$

Diameter of Stent in Segment n+1:

$$SegDia_{n+1} = \sqrt[exp]{SegDia_n^{exp} + \partial_n}$$

The segment diameter above provides a delta measurement by which the boundary of an upper and lower taper of the target stent profile undergoes a stepwise change in the amount of such as delta measurement as the tapered boundaries are generated across the vessel segment. This tapering and information about healthy regions in the blood vessel can be used to interpolate a lumen profile that is representative of a healthy vessel—one achievable with proper stent expansion across the length of the stent.

After the stent has been placed, the stent detection algorithm locates the stented lumen region. The lumen profile in the stented region is compared with a second lumen profile generated by interpolating between a first and a second position of the blood vessel shift from the detected endpoints of the stents, the distances D1 and D2. The landing zones of the stent, which correspond to its respective endpoints, are correlated with healthy tissue in the blood vessel. By shifting over the distance D1 and D2 relative to the end points of the detected stent, two healthy lumen diameters, areas, chords, etc. can be selected. These two selected distances along with the tapering profile of the blood vessel and other blood vessel parameters and models and be used to interpolate the tapering profile 290, which can be shown in one or more lumen profile views.

Any over or under expansion can be determined by comparing the two lumen profile views, the measured and the interpolated or ratios or other metrics based on geometric values at the same position for each profile. For each point along the stent, the ratio of a value such as a diameter or area from the interpolated lumen profile view, which is indicative of the result from ideal stent expansion, can be generated relative to the corresponding area or diameter value of the lumen profile generated using the detected stent struts. The profile generated from the detected stent struts is representative of the levels of expansion obtained when a balloon was used to initially expand the stent for positioning in the blood vessel. The stent is placed at target landing zones. From the selection of these landing zones, in one embodiment, the correlation with such zones being selected that are healthy has been used as a measurable parameter to address the technical challenge of assessing stent expansion. These and other metrics can be used to generate tools for end users as part of the stent expansion assessment and correction.

The system and software-based method described herein can process frames of optical coherence tomography data obtained with respect to a blood vessel such that a stent disposed in the blood vessel can be evaluated or otherwise characterized. In one embodiment, each cross-sectional image can constitute a frame of OCT image data. For example, in one embodiment such a stent is identified on a graphic user interface showing a three-dimensional or two-dimensional image of the blood vessel generated using collected image data.

The software modules and stented vessel expansion evaluation and display features described herein can be implemented using a non-transitory computer-readable storage medium. In one embodiment, the non-transitory computer-readable storage medium stores a program that, when executed by a computing device, causes the computing device to perform a method for processing or otherwise operating upon intravascular image data and intravascular parameters. Each method can include one or more of the steps outlined herein.

The system and software-based method described herein can process frames of optical coherence tomography data obtained with respect to a blood vessel such that a stent disposed in the blood vessel can be evaluated or otherwise characterized. In one embodiment, each cross-sectional image can constitute a frame of image data. For example, in one embodiment such a stent is identified on a graphic user interface showing a three-dimensional or two-dimensional image of the blood vessel generated using collected image data.

The software modules and stented vessel expansion evaluation and display features described herein can be implemented using a non-transitory computer-readable storage medium. In one embodiment, the non-transitory computer-readable storage medium stores a program that, when executed by a computing device, causes the computing device to perform a method for processing or otherwise operating upon intravascular image data and intravascular parameters. Each method can include one or more of the steps outlined herein. In one embodiment, the stent expansion threshold ranges from about 90% to about 100%. In one embodiment, the stent expansion threshold ranges from about 80% to about 90%. In one embodiment, the stent expansion threshold ranges from about 85% to about 95%. In one embodiment, the stent expansion threshold ranges from about 75% to about 85%.

Non-Limiting Software Features and Embodiments for Implementing Stent Expansion Assessment and User Feedback In part, the disclosure relates to computer-based methods, systems and devices for visualizing stents. In one embodiment, the disclosure relates to methods to evaluate the expansion of a stented vessel and whether further expansion is needed or if stent repositioning is needed. These methods of evaluation can include displaying one or more views of a stent in various states such as an expanded state relative to the blood vessel and comparing the imaged stent relative to one or more selected stent profiles. In one embodiment, the method is performed automatically. The methods of the disclosure can be implemented using software such as stent profile analysis software which can include stent planning software and lesion preparation software (or vice versa).

A stent may be selected for placement using OCT, IVUS, angiography or other probe data obtained relative to the unstented vessel segment and then subsequently compared to stented blood vessel. The stented and unstented stages of stent planning can be subsequently displayed longitudinally or in a cross-sectional view in expanded or unexpanded state as a part of a one or more graphic user interface(s) (GUI). Such an interface can include one or more views of a blood vessel generated using distance measurements obtained using an OCT system, IVUS system, angiography system or other data collection systems.

The second pullback can be performed just after stenting so that further inflation or reposition or removal can be performed. These can result in valuable time being saved and a need for a follow up procedure.

An exemplary image processing pipeline 350 for transforming collected OCT data into two dimensional and three dimensional views of blood vessels and stents and comparing profiles relative to stent deployment is depicted in FIG. 8. The image data processing pipeline or any of the methods described herein are stored in memory and executed using one or more computing devices such as a processor, device, or other integrated circuit. In one embodiment, the computing device 340 includes or accesses software modules or programs, such as a side branch detection module, a guide wire detection module, a lumen detection module, stent deployment analysis software, stent expansion analysis and display software, such as software 67 of FIG. 1A, and other software modules. The software modules or programs can include an image data processing pipeline or component modules thereof and one or more graphical user interfaces (GUI).

As shown, in FIG. 8, one or more displays 346 can be used for showing information such as cross-sectional and longitudinal views of a blood vessel generated using collected intravascular data and angiography data such the vessel segments views and profiles in shown and disclosed herein. These displays 346 can be arranged as shown in FIG. 1B. This information can be displayed using one or more graphic user interface(s) (GUI). In addition, this information can include, without limitation, cross-sectional scan data, longitudinal scans, lumen profiles, VRR values, FFR values, stents, areas of malapposition, lumen border, jailed side branches, and other images or representations of a blood vessel or the underlying distance measurements obtained using an system 355 and data collection probe. In one embodiment, the computing device 340 can also include software or programs 344, which can be stored in one or more memory devices, configured to identify target stent profiles, lumen contours, and stent expansion values and targets and other blood vessel features such as with text, arrows, color coding, highlighting, contour lines, or other suitable human or machine readable indicia. The software module pipeline can include and features to support and provide for stent expansion analysis and display. Various indicia can be applied via indicia application module 370 to emphasize and distinguish any and all of the detected and generated arterial image data and generated profile views and stent-related parameters.

Once the image data is obtained with a probe for OCT or IVUS image data or other imaging system, such as angiography system, and stored in memory; it can be processed to generate information such as a cross-sectional, a longitudinal, and/or a three-dimensional view of the blood vessel along the length of the pullback region or a subset thereof. These views can be depicted as part of the user interface depicted in various figures. The images of the blood vessel generated using the distances measurements obtained from the OCT system provide information about the blood vessel and objects disposed therein.

As shown, the pipeline can receive post stent deployment pullback data 352 which would come after an initial pullback to image a blood vessel. User selections can be received via a GUI and the stent plan data can be transferred to stent profile or stent deployment analysis software such as software 67 in FIG. 1A. The guide wire 354, side branch detection 356, stent detection 358, and lumen detection modules 360 can operate on the post stent deployment pullback data which may be collected scan lines. The stent expansion analysis and display software 362 can perform various steps as described herein such as evaluating detected stents relative to detected lumen contours, calculating stent expansion, calculating MSA, measuring stent parameters and showing expansion levels of stent at different frames along artery and other features and methods as disclosed herein. In addition, the pipeline can include co-registration software for co-registering angiography data and intravascular data to show stent expansion data relative to angiography data. In one embodiment, stent expansion is evaluated using data from two or more intravascular imaging pullback sessions in which a probe is pulled back through a section of an artery.

The following description is intended to provide an overview of device hardware and other operating components suitable for performing the methods of the disclosure described herein. This description is not intended to limit the applicable environments or the scope of the disclosure. Similarly, the hardware and other operating components may be suitable as part of the apparatuses described above. The disclosure can be practiced with other system configurations, including personal computers, multiprocessor systems, microprocessor-based or programmable electronic device, network PCs, minicomputers, mainframe computers, and the like. The disclosure can also be practiced in distributed computing environments where tasks are performed by remote processing devices that are linked through a communications network such as in different rooms of a catheter or cath lab.

Some portions of the detailed description are presented in terms of algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as apparent from the following discussion, it is appreciated that throughout the description, discussions utilizing terms such as "processing" or "computing" "overlaying" or "searching" or "detecting" or "measuring" or "calculating" or "comparing" "generating" or "determining" or "displaying," or Boolean logic or other set related operations or the like, refer to the action and processes of a computer system, or electronic device, that manipulates and transforms data represented as physical (electronic) quantities within the computer system's or electronic devices' registers and memories into other data similarly represented as physical quantities within electronic memories or registers or other such information storage, transmission or display devices.

The present disclosure, in some embodiments, also relates to apparatus for performing the operations herein. This apparatus may be specially constructed for the required purposes, or it may comprise a general purpose computer selectively activated or reconfigured by a computer program stored in the computer.

Embodiments of the disclosure may be embodied in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other programmable logic device), discrete components, integrated circuitry (e.g., an Application Specific Integrated Circuit (ASIC)), or any other means including any combination thereof. In a typical embodiment of the present disclosure, some or all of the processing of the data collected using an OCT probe and the processor-based system is implemented as a set of computer program instructions that is converted into a computer executable form, stored as such in a computer readable medium, and executed by a microprocessor under the control of an operating system. Thus, query response and input data are transformed into processor understandable instructions suitable for generating imaging data, detecting lumen borders, detecting stent struts, comparing measured perpendicular distances relative to set thresholds, and otherwise performing image comparison, signal processing, lumen detection, stent detection, and comparison of detected stents, and other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed below in more detail. As used herein a module refers to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as OCT scan data, IVUS scan data, interferometer signal data, target stent profiles, post-stent deployment lumen profiles and images, interpolated lumen profile views indicative of fully expanded stents, ratios of geometric values of expanded stent-based lumen profile to fully expanded lumen profile, stent expansion level indicia (color, hatching, etc.), highlighting/emphasizing pixel properties, side branch locations, side branch diameters, stent expansion percentages or fractions, pre-stenting FFR values, post-stenting FFR values, and other pre and post stenting values and other information of interest.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the disclosure described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the disclosure.

A storage medium may be non-transitory or include a non-transitory device. Accordingly, a non-transitory storage medium or non-transitory device may include a device that is tangible, meaning that the device has a concrete physical form, although the device may change its physical state. Thus, for example, non-transitory refers to a device remaining tangible despite this change in state.

The aspects, embodiments, features, and examples of the disclosure are to be considered illustrative in all respects and are not intended to limit the disclosure, the scope of which is defined only by the claims. Other embodiments, modifications, and usages will be apparent to those skilled in the art without departing from the spirit and scope of the claimed disclosure.

The use of headings and sections in the application is not meant to limit the disclosure; each section can apply to any aspect, embodiment, or feature of the disclosure Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" or "substantially" is before a quantitative value, the present teachings also include the specific quantitative value itself, unless specifically stated otherwise. The terms "about" and "substantially" as used herein, refer to variations in a numerical quantity that can occur, for example, through measuring or handling procedures in the real world; through inadvertent error in these procedures; through differences/faults in the manufacture of materials, such as composite tape, through imperfections; as well as variations that would be recognized by one in the skill in the art as being equivalent so long as such variations do not encompass known values practiced by the prior art. Typically, the terms "about" and "substantially" means greater or lesser than the value or range of values stated by $\frac{1}{10}$ of the stated value, e.g., ±10%.

It should be understood that the order of steps or order for performing certain actions is immaterial so long as the present teachings remain operable. Moreover, two or more steps or actions may be conducted simultaneously.

The use of headings and sections in the application is not meant to limit the disclosure; each section can apply to any aspect, embodiment, or feature of the disclosure. Only those claims which use the words "means for" are intended to be interpreted under 35 USC 112, sixth paragraph. Absent a recital of "means for" in the claims, such claims should not be construed under 35 USC 112. Limitations from the specification are not intended to be read into any claims, unless such limitations are expressly included in the claims.

When values or ranges of values are given, each value and the end points of a given range and the values there between may be increased or decreased by 20%, while still staying within the teachings of the disclosure, unless some different range is specifically mentioned.

Where a range or list of values is provided, each intervening value between the upper and lower limits of that range or list of values is individually contemplated and is encompassed within the disclosure as if each value were specifically enumerated herein. In addition, smaller ranges between and including the upper and lower limits of a given range are contemplated and encompassed within the disclosure. The listing of exemplary values or ranges is not a disclaimer of other values or ranges between and including the upper and lower limits of a given range.

It is to be understood that the figures and descriptions of the disclosure have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the disclosure, a single component may be replaced by multiple components, and multiple components may be replaced by a single component, to provide an element or structure or to perform a given function or functions. Except where such substitution would not be operative to practice certain embodiments of the disclosure, such substitution is considered within the scope of the disclosure.

The examples presented herein are intended to illustrate potential and specific implementations of the disclosure. It can be appreciated that the examples are intended primarily for purposes of illustration of the disclosure for those skilled in the art. There may be variations to these diagrams or the operations described herein without departing from the spirit of the disclosure. For instance, in certain cases, method steps or operations may be performed or executed in differing order, or operations may be added, deleted or modified.

What is claimed is:

1. A method of evaluating stent expansion in a blood vessel defining a lumen comprising:
    scanning a stented blood vessel using a first imaging system to obtain a first set of blood vessel image data;
    storing, by one or more processors, the first set of blood vessel image data in an electronic memory device in electronic communication with the first imaging system;
    detecting, by the one or more processors, stent struts along a length of the stented vessel using one more software modules;
    generating, by the one or more processors, a first representation of a segment of the blood vessel indicative of a level of stent expansion;
    determining, by the one or more processors, using the detected stent struts, a first end of the stent and a second end of the stent;
    defining a first offset distance (D1) from the first end of the stent and a second offset distance from the second end of the stent (D2);
    generating, by the one or more processors, a second representation of the segment of the blood vessel using D1 and D2 in combination with a tapering profile of the segment; and
    determining, by the one or more processors, a level of target stent expansion along blood vessel segment by comparing a first value associated with the first representation with a second value associated with the second representation at different positions along the length of the segment.

2. The method of claim 1, wherein the blood vessel received one or more stents during a first procedure, wherein the scanning of the stented blood vessel is performed as a diagnostic analysis as an extension of the first procedure.

3. The method of claim 1, wherein the first representation is a first lumen profile of stented blood vessel, wherein the lumen profile is generated based upon actual expansion level of stent along length of the segment.

4. The method of claim 3, wherein the second representation is a second lumen profile generated based on a geometric value of blood vessel at each of D1 and D2, wherein the second lumen profile is interpolated based on such geometric values and the tapering profile of the blood vessel.

5. The method of claim 4 further comprising detecting one or more side branches along the segment, wherein interpolation of the second lumen profile is generated using one or more detected side branches.

6. The method of claim 4 wherein the geometric value of blood vessel is selected from the group consisting of an area, a diameter, a chord, a Euclidean distance metric, and a volume.

7. The method of claim 4, wherein determining level of target stent expansion further comprises determining degree of stent expansion relative to a stent expansion threshold using ratio of the first value of first lumen profile to the second value of the second lumen profile at a plurality of positions along the segment.

8. The method of claim 1, wherein the first representation comprises one or more views of the blood vessel, wherein one or more views of the blood vessel display detected stent struts and a representation of the lumen of the blood vessel.

9. The method of claim 1, wherein the scanning of the stented blood vessel is performed using optical coherence tomography; angiography; ultrasound; x-rays; optical imaging; pressure sensing; flow sensing; and tomographic imaging.

10. The method of claim 1, wherein the scanning of the stented blood vessel is performed using an intravascular data collection probe pulled back through the blood vessel.

11. The method of claim 1, wherein the scanning of the stented blood vessel is performed using one or more of shadows or reflections from the first set of blood vessel image data.

12. The method of claim 1, wherein D1 and D2 are selected based upon proximity to user selected target landing zones when stent was placed.

13. The method of claim 1 further comprising generating, using one or more computing devices, a blood vessel lumen profile after deployment of a stent in the blood vessel.

14. The method of claim 1 further comprising displaying one or more views of the blood vessel and/or the first vessel representation and displaying one or more visual cues indicating regions of stent under expansion along length of blood vessel segment.

15. The method of claim 1 further comprising detecting side branches along a length of a segment of blood vessel and displaying side branches relative to lumen.

16. The method of claim 15, wherein the side branches are displayed as dots, ellipses, circles, or other shapes relative to the first representation.

17. The method of claim 1, wherein the first representation is displayed using user interface of imaging system.

18. The method of claim 1, further comprising scanning the blood vessel with an angiography system and co-registering angiography data with detected stent struts and a first visual cue indicative of stent expansion above a stent expansion threshold and a second visual cue indicative of stent expansion below the stent expansion threshold.

19. The method of claim 1, further comprising visually emphasizing region of first representation that includes stent.

20. The method of claim 19, wherein user interface emphasizes the region by changing contrast, intensity, color of another visual element relative to the region.

21. The method of claim 4 wherein D1 and D2 are selected from a distance that ranges from about 0.1 mm to about 1.0 mm.

22. The method of claim 1, further comprising detecting one or more side branches along segment, wherein determining tapering profile of the segment comprises adjusting profile based on diameter of at least one detected side branch.

23. The method of claim 1, further comprising determining a minimum expansion frame and displaying an indication of the minimum expansion frame.

24. An processor-based system for evaluating a stent expansion in a stented blood vessel comprising:
    one or more memory devices; and
    one or more processors in communication with the memory device, wherein the memory device comprises instructions executable by the one or more processors to cause the computing device to:

store a first set of blood vessel image data in an electronic memory device in electronic communication with a first imaging system, the first set of blood vessel image data generated by scanning the blood vessel with the first imaging system;

detecting stent struts along a segment of the stented vessel;

generate a first representation of a segment of the blood vessel indicative of a level of stent expansion;

determine using the detected stent struts, a first end of the stent and a second end of the stent;

define a first offset distance (D1) from the first end of the stent and a second offset distance from the second end of the stent (D2);

generate a second representation of the segment of the blood vessel using D1 and D2 in combination with tapering profile of the segment; and determine level of target stent expansion along blood vessel segment by comparing a first value associated with the first representation with a second value associated with the second representation at different positions along the segment.

25. The system of claim 24 wherein the first value is a first area or a first diameter, wherein the second value is second area or a second diameter.

\* \* \* \* \*